(12) United States Patent
Haller et al.

(10) Patent No.: US 8,216,268 B2
(45) Date of Patent: Jul. 10, 2012

(54) INTRAGASTRIC BAG FOR TREATING OBESITY

(75) Inventors: Frederick B. Haller, Winston-Salem, NC (US); John A. Karpiel, Winston-Salem, NC (US); Donagh O'Sullivan, Limerick (IE); Brian K. Rucker, King, NC (US); Maximiliano Soetermans, Pinnacle, NC (US); William D. Voorhees, III, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1043 days.

(21) Appl. No.: 11/643,436

(22) Filed: Dec. 21, 2006

(65) Prior Publication Data

US 2007/0276428 A1    Nov. 29, 2007

Related U.S. Application Data

(60) Provisional application No. 60/752,795, filed on Dec. 22, 2005.

(51) Int. Cl.
    *A61M 29/00*    (2006.01)
(52) U.S. Cl. .................................... 606/196; 606/151
(58) Field of Classification Search .................. 606/192, 606/191, 196, 151, 153, 157; 623/23.65, 623/23.64
    See application file for complete search history.

(56) References Cited

U.S. PATENT DOCUMENTS

| | | | |
|---|---|---|---|
| 2,508,690 A | 5/1950 | Schmerl | |
| 4,085,757 A * | 4/1978 | Pevsner | 606/195 |
| 4,133,315 A | 1/1979 | Berman et al. | |
| 4,134,405 A | 1/1979 | Smit | |
| 4,246,893 A | 1/1981 | Berson | |
| 4,315,509 A | 2/1982 | Smit | |
| 4,403,604 A | 9/1983 | Wilkinson et al. | |
| 4,416,267 A | 11/1983 | Garren et al. | |
| 4,485,805 A | 12/1984 | Foster, Jr. | |
| 4,558,699 A | 12/1985 | Bashour | |
| 4,607,618 A | 8/1986 | Angelchik | |
| 4,694,827 A | 9/1987 | Weiner et al. | |
| 4,696,288 A | 9/1987 | Kuzmak et al. | |
| 4,723,547 A | 2/1988 | Kullas et al. | |
| 4,803,985 A | 2/1989 | Hill | |
| 4,878,905 A | 11/1989 | Blass | |
| 4,899,747 A * | 2/1990 | Garren et al. | 606/192 |

(Continued)

FOREIGN PATENT DOCUMENTS

EP    0137 878    11/1983

(Continued)

*Primary Examiner* — Ryan Severson
*Assistant Examiner* — Tin Nguyen
(74) *Attorney, Agent, or Firm* — Brinks Hofer Gilson & Lione

(57) ABSTRACT

An apparatus and method comprising at least one intragastric member made of a digestive-resistant or substantially indigestible material that is introduced into a bag located in the gastric lumen of a mammal for the treatment of obesity. One or more intragastric members are loaded into a delivery tube in a partially compacted first configuration and delivered to an overtube. The overtube includes a proximal end, a distal end and a lumen configured to receive the intragastric members in the first configuration for delivery to the bag located in the gastric lumen wherein the intragastric member is expanded to a second configuration. The apparatus further comprises a constraining element engaged with the bag to secure the intragastric member upon delivery into the gastric lumen.

23 Claims, 21 Drawing Sheets

U.S. PATENT DOCUMENTS

| | | |
|---|---|---|
| 4,925,446 A | 5/1990 | Garay et al. |
| 4,952,339 A | 8/1990 | Temus et al. |
| 5,129,915 A | 7/1992 | Cantenys |
| 5,234,454 A | 8/1993 | Bangs |
| 5,246,456 A | 9/1993 | Wilkinson |
| 5,306,300 A | 4/1994 | Berry |
| 5,327,914 A | 7/1994 | Shlain |
| 5,345,949 A | 9/1994 | Shlain |
| 5,868,141 A | 2/1999 | Ellias |
| 5,938,669 A | 8/1999 | Klaiber et al. |
| 5,993,473 A | 11/1999 | Chan et al. |
| 6,067,991 A | 5/2000 | Forsell |
| 6,210,347 B1 | 4/2001 | Forsell |
| 6,427,089 B1 | 7/2002 | Knowlton |
| 6,450,946 B1 | 9/2002 | Forsell |
| 6,454,699 B1 | 9/2002 | Forsell |
| 6,460,543 B1 | 10/2002 | Forsell |
| 6,511,490 B2 | 1/2003 | Robert |
| 6,540,789 B1 | 4/2003 | Silverman et al. |
| 6,558,400 B2 | 5/2003 | Deem et al. |
| 6,627,206 B2 | 9/2003 | Lloyd |
| 6,656,194 B1 | 12/2003 | Gannoe et al. |
| 6,675,809 B2 | 1/2004 | Stack et al. |
| 6,676,674 B1 | 1/2004 | Dudai |
| 6,733,512 B2 | 5/2004 | McGhan |
| 6,740,121 B2 | 5/2004 | Geitz |
| 6,746,460 B2 | 6/2004 | Gannoe et al. |
| 6,755,869 B2 | 6/2004 | Geitz |
| 6,802,868 B2 | 10/2004 | Silverman et al. |
| 6,845,776 B2 | 1/2005 | Stack et al. |
| 6,879,859 B1 | 4/2005 | Boveja |
| 6,916,326 B2 | 7/2005 | Benchetrit |
| 6,946,002 B2 | 9/2005 | Geitz |
| 6,981,980 B2 | 1/2006 | Sampson et al. |
| 6,994,715 B2 | 2/2006 | Gannoe et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,054,690 B2 | 5/2006 | Imran |
| 7,056,305 B2 | 6/2006 | Garza Alvarez |
| 7,066,945 B2 | 6/2006 | Hashiba et al. |
| 7,090,699 B2 | 8/2006 | Geitz |
| 7,097,665 B2 | 8/2006 | Stack et al. |
| 7,112,186 B2 | 9/2006 | Shah |
| 7,121,283 B2 | 10/2006 | Stack et al. |
| 7,152,607 B2 | 12/2006 | Stack et al. |
| 7,172,613 B2 | 2/2007 | Wazne |
| 7,175,638 B2 | 2/2007 | Gannoe et al. |
| 7,177,693 B2 | 2/2007 | Starkebaum |
| 2001/0011543 A1 | 8/2001 | Forsell |
| 2002/0188354 A1 | 12/2002 | Peghini |
| 2003/0049325 A1 | 3/2003 | Suwelack et al. |
| 2003/0078611 A1 * | 4/2003 | Hashiba et al. ............... 606/191 |
| 2003/0109892 A1 | 6/2003 | Deem et al. |
| 2003/0120265 A1 | 6/2003 | Deem et al. |
| 2003/0158564 A1 | 8/2003 | Benchetrit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0044353 A1 | 3/2004 | Gannoe |
| 2004/0044354 A1 | 3/2004 | Gannoe et al. |
| 2004/0049209 A1 | 3/2004 | Benchetrit |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0153106 A1 | 8/2004 | Dudai |
| 2004/0158331 A1 | 8/2004 | Stack et al. |
| 2004/0186503 A1 | 9/2004 | DeLegge |
| 2004/0220682 A1 | 11/2004 | Levine et al. |
| 2004/0243152 A1 | 12/2004 | Taylor et al. |
| 2005/0049718 A1 | 3/2005 | Dann et al. |
| 2005/0096750 A1 | 5/2005 | Kagan et al. |
| 2005/0149141 A1 | 7/2005 | Starkebaum |
| 2005/0149142 A1 | 7/2005 | Starkebaum |
| 2005/0177181 A1 | 8/2005 | Kagan et al. |
| 2005/0192531 A1 | 9/2005 | Birk |
| 2005/0192614 A1 | 9/2005 | Binmoeller |
| 2005/0209653 A1 | 9/2005 | Herbert et al. |
| 2005/0222637 A1 | 10/2005 | Chen |
| 2005/0222638 A1 | 10/2005 | Foley et al. |
| 2005/0240239 A1 | 10/2005 | Bojeva et al. |
| 2005/0240279 A1 | 10/2005 | Kagan et al. |
| 2005/0245957 A1 | 11/2005 | Starkebaum et al. |
| 2005/0246037 A1 | 11/2005 | Starkebaum |
| 2005/0250979 A1 | 11/2005 | Coe |
| 2005/0256587 A1 | 11/2005 | Egan |
| 2005/0267405 A1 | 12/2005 | Shah |
| 2006/0015151 A1 | 1/2006 | Aldrich |
| 2006/0020247 A1 | 1/2006 | Kagan et al. |
| 2006/0030949 A1 | 2/2006 | Geitz |
| 2006/0074450 A1 | 4/2006 | Boveja et al. |
| 2006/0079944 A1 | 4/2006 | Imran |
| 2006/0089571 A1 | 4/2006 | Gertner |
| 2006/0129027 A1 | 6/2006 | Catona |
| 2006/0129094 A1 | 6/2006 | Shah |
| 2006/0161172 A1 | 7/2006 | Levine et al. |
| 2006/0206063 A1 | 9/2006 | Kagan et al. |
| 2006/0206064 A1 | 9/2006 | Kagan et al. |
| 2006/0206160 A1 | 9/2006 | Cigaina et al. |
| 2006/0249165 A1 | 11/2006 | Silverman et al. |
| 2006/0253142 A1 | 11/2006 | Bjerken |
| 2006/0257444 A1 | 11/2006 | Tropsha et al. |
| 2006/0257445 A1 | 11/2006 | Tropsha et al. |
| 2006/0257446 A1 | 11/2006 | Tropsha et al. |
| 2006/0282107 A1 | 12/2006 | Hashiba et al. |
| 2006/0293742 A1 | 12/2006 | Dann et al. |
| 2007/0004963 A1 | 1/2007 | Benchetrit |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0038308 A1 | 2/2007 | Geitz |

FOREIGN PATENT DOCUMENTS

| | | | |
|---|---|---|---|
| WO | WO 8700034 A2 * | 1/1987 | |
| WO | WO 2004/084763 A2 | 10/2004 | |
| WO | WO 2005/107641 A2 | 11/2005 | |

* cited by examiner

INTRAGASTRIC BAG FOR TREATING OBESITY

RELATED APPLICATIONS

This application claims priority to provisional application No. 60/752,795 filed on Dec. 22, 2005, the entire disclosure of which is incorporated by reference herein.

TECHNICAL FIELD

This invention relates to medical devices, and more particularly to obesity treatment devices that can be placed in the stomach of a patient to reduce the size of the stomach reservoir or to place pressure on the inside surface of the stomach.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition. More invasive approaches have been available which have yielded good results in many patients. These include surgical options such as bypass operations or gastroplasty. However, these procedures carry high risks and are therefore not appropriate for most patients.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These balloons are typically cylindrical or pear-shaped, generally range in size from 200-500 ml or more, are made of an elastomer such as silicone, polyurethane, or latex, and are filled with air, water, or saline. While some studies demonstrated modest weight loss, the effects of these balloons often diminished after three or four weeks, possibly due to the gradual distension of the stomach or the fact that the body adjusted to the presence of the balloon. Other balloons include a tube exiting the nasal passage that allows the balloon to be periodically deflated and re-insufflated to better simulate normal food intake. However, the disadvantages of having an inflation tube exiting the nose are obvious.

The experience with balloons as a method of treating obesity has provided uncertain results, and has been frequently disappointing. Some trials failed to show significant weight loss over a placebo, or were ineffective unless the balloon placement procedure was combined with a low-calorie diet. Complications have also been observed, such as gastric ulcers, especially with use of fluid-filled balloons, and small bowel obstructions caused by deflated balloons. In addition, there have been documented instances of the balloon blocking off or lodging in the opening to the duodenum, wherein the balloon may act like a ball valve to prevent the stomach contents from emptying into the intestines.

Unrelated to the above-discussed methods for treating obesity, it has been observed that the ingestion of certain indigestible matter, such as fibers, hair, fuzzy materials, etc., can collect in the stomach over time, and eventually form a mass called a bezoar. In some patients, particularly children and the mentally handicapped, bezoars often result from the ingestion of plastic or synthetic materials. In many cases, bezoars can cause indigestion, stomach upset, or vomiting, especially if allowed to grow sufficiently large. It has also been documented that certain individuals having bezoars are subject to weight loss, presumably due to the decrease in the size of the stomach reservoir. Although bezoars may be removed endoscopically, especially in conjunction with a device known as a bezotome or bezotriptor, they, particularly larger ones, often require surgery.

What is needed is an intragastric member that provides the potential weight loss benefits of a bezoar or intragastric balloon without the associated complications. Ideally, such a device should be well-tolerated by the patient, effective over a long period of time, sizable for individual anatomies, and easy to place and retrieve. The device will also provide the benefit of short-term weight loss thereby preparing the patient to safely undergo subsequent medical procedures involving surgery.

SUMMARY OF THE INVENTION

The foregoing problems are solved and a technical advance is achieved by an illustrative obesity treatment apparatus comprising at least one intragastric member such as an artificial bezoar made of a digestive-resistant or substantially indigestible material that is introduced into a bag located in the gastric lumen of a mammal in a first configuration. The intragastric member is typically inserted into a bag located in the gastric lumen in a partially compacted configuration, whereby it is then manipulated into, or allowed to assume, a second expanded configuration sufficiently large to maintain the bag within the reservoir of the stomach during normal activities and not be passed through the pylorus and into the intestines. Another advance is that the present invention can be effective at a smaller volume within the stomach compared to existing intragastric members, such as balloons.

In one aspect of the invention, the obesity treatment apparatus comprises a bag disposed within the gastric lumen of a mammal and one or more intragastric members disposed within the bag. The intragastric members are sufficiently small to permit introduction of the one or more intragastric members into the bag. When the one or more intragastric members are disposed within the bag, the bag is configured to prevent the apparatus from passing through the mammal's pylorus. The one or more intragastric members are expandable from a first configuration to a second configuration upon contacting gastric fluid in the gastric lumen. Alternatively, the intragastric members may be self expanding or may be expanded upon the injection of a fluid such as saline.

In another aspect of the invention, the obesity treatment apparatus comprises a plurality of intragastric members delivered to a bag. The plurality of intragastric members may be coupled together in a set or grouping within the bag located in the gastric lumen. The intragastric members may be individually loaded into the bag, and then grouped together using a coupling mechanism. Additional components may also be used with the coupling mechanism to facilitate placement of the set and/or separation of the individual intragastric members. For example, specially configured plastic or metal pieces can be attached to the line bundling the set of intragastric members together to enhance visibility of the line for cutting with an endoscopic scissor or scalpel, or to provide a hard surface against which the cutting instrument can be applied to more easily sever the line. Irrespective of whether the obesity treatment apparatus includes a single intragastric member, or a coupling of intragastric members, the principal requirement is that, once in the bag located in the gastric lumen, it attains a shape and size that prevents the bag from passing through or lodging in the pyloric sphincter. The bag may further include an inner member to seal the inner reservoir of the bag after delivery of the intragastric member into the bag. The bag may be secured with any suitable constraining means, such as a stopper, after the intragastric member is delivered into the bag. The bag may further comprise a porous or non-porous digestive resistant or substantially indigestible material, wherein the material can be woven or non-woven. The bag may also include one or more openings located along the surface, such as an open mesh configuration, that permits the passage of fluids therethrough.

In another aspect of the invention, the obesity treatment device includes a delivery system to place the intragastric members within a bag located in the gastric lumen. In one embodiment, a bag is delivered to the gastric lumen. Then, one or more intragastric members are mounted on a delivery tube and secured with a releasing mechanism, such as a nylon thread, extending through the passageway of the delivery tube. A metal wire or loop is then withdrawn, severing the thread(s) and releasing the intragastric member(s) into the bag located in the gastric lumen. The individual intragastric members are then secured with a device such as a rubber patch pushed by an introduced metal tube or similar device.

Other delivery systems of the present invention involve constraining the intragastric members, then releasing them into a bag within the gastric lumen. These can include pushing the intragastric member(s) from an outer delivery catheter, typically by use of a pusher member within the delivery catheter passageway. Other methods include constraining the intragastric member(s) with a splittable or dissolvable film or sheath that allows that device to be deployed in a compact configuration, then the intragastric member is allowed to expand when the outer wrapping or sheath is split by the operator, or when the outer wrapping or sheath is allowed to dissolve away over time in the stomach. The dissolvable film or sheath of the intragastric member comprises a material selected from the group consisting of cellulose, gelatin and glycerin.

In still yet another aspect of the invention, the intragastric members can be precoupled together with a coupling mechanism, such as a nylon fishing line, prior to introduction into the gastric lumen. Because the volume of the grouping in the stomach increases over time due to mucous accumulation or other factors, a single device having the overall size of the grouping (e.g., four members grouped together) may not be readily removed. However, by severing the line comprising the coupling mechanism, the individual intragastric members of the grouping can be removed one at a time by using an endoscope and retrieval device.

In still yet another aspect of the invention, the obesity treatment apparatus can comprise one or more intragastric members made of a digestive-resistant material loaded onto a delivery tube in a partially compacted first configuration, wherein the assembly is delivered through an overtube. The overtube includes a proximal end, a distal end, and a lumen configured to receive the intragastric members in the first configuration for delivery to the gastric lumen wherein the digestive-resistant material of the intragastric member is expanded to a second configuration within the bag.

In still yet another aspect of the present invention, the obesity treatment apparatus can comprise a plurality of intragastric members having a small bead or ball-like structure deployed into a bag located in the stomach. The intragastric members can be inserted into the bag separately or together to displace volume in the gastric lumen. The bag is then secured by pushing a stopper or similar device onto the opening of the bag. Additionally, the intragastric members can be delivered utilizing an elastic band attached to the opening of the bag which is inserted over an overtube wherein the remainder of the bag is inverted into the lumen of the overtube. The intragastric members are subsequently pushed into the bag until the bag is filled. A coaxial outer tube or similar device can be utilized to remove the elastic band from the overtube and thereby secure the bag with the elastic band. The intragastric members may be removed by rupturing the bag resulting in the intragastric members passing through the gastrointestinal tract of the patient. Alternatively, the intragastric members can be removed by rupturing the bag and utilizing an overtube to suction the intragastric members from the bag and subsequently removing the bag through the overtube or endoscope with forceps or similar device. Further, the intragastric members can include a color coding to allow the intragastric members to be easily identified if the bag is prematurely ruptured.

In still yet another aspect of the invention, a method of treatment of obesity in mammals can comprise the steps of positioning a bag within the gastric lumen of a mammal and loading at least one intragastric member into the bag, wherein when the at least one intragastric member is disposed within the bag, the bag is prevented from passing through the mammal's pylorus. The method further includes the additional step of positioning a delivery tube comprising the at least one intragastric member within a lumen of an overtube and advancing the at least one intragastric member through the lumen of the overtube into the bag located in the gastric lumen of the mammal. The method also includes the step of securing the at least one intragastric member in the bag located in the gastric lumen of the mammal. Upon delivery, the at least one intragastric member may be self expanding, may be expanded upon the injection of a fluid such as saline, or may be expanded upon contacting gastric fluid of the gastric lumen.

In still yet another aspect of the invention, a method of treatment of obesity in mammals can comprise the steps of positioning a bag within the gastric lumen of a mammal and loading a plurality of intragastric members into the bag, wherein when the plurality of intragastric members are disposed within the bag, the bag is prevented from passing through the mammal's pylorus. The method further includes the additional step of positioning a delivery tube comprising the plurality of intragastric members within a lumen of an overtube and advancing the plurality of intragastric members through the lumen of the overtube into the gastric lumen of the mammal. The method also includes the step of securing the plurality of intragastric members in the bag located in the gastric lumen of the mammal.

These and other advantages, as well as the invention itself, will become apparent in the details of construction and operation as more fully described below. Moreover, it should be appreciated that several aspects of the invention can be used with other types of intragastric devices or procedures used for the treatment of obesity.

BRIEF DESCRIPTION OF THE DRAWINGS

Several embodiments of the present invention will now be described by way of example with reference to the accompanying drawings, in which.

DETAILED DESCRIPTION OF THE INVENTION

Figure 1:
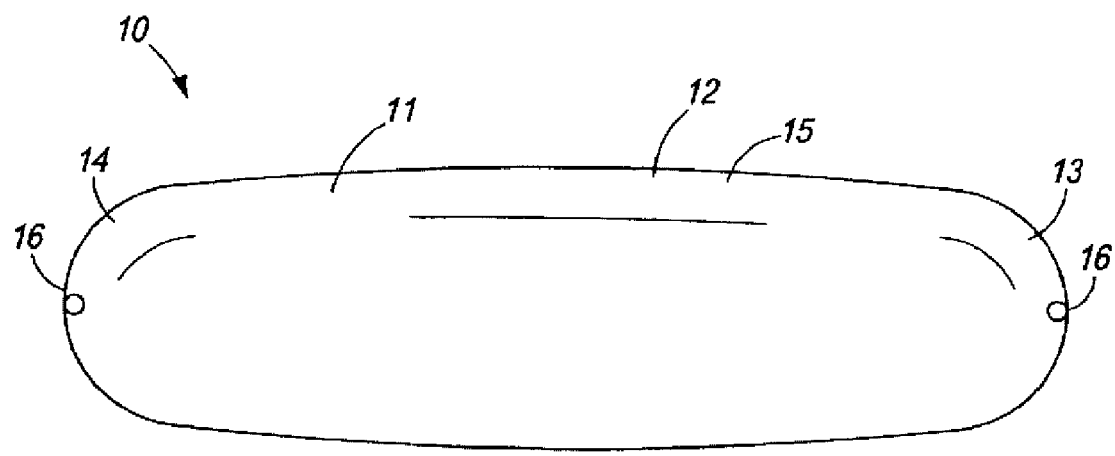
FIG. 1 depicts a pictorial view of an intragastric member of the present invention.

The obesity treatment apparatus 10 of the present invention depicted in FIGS. 1-26 comprise one or more intragastric members 11, each comprising a digestive-resistant or indigestible member 12 sized and configured such that the intragastric member 11 can be delivered to a bag 30 placed into the stomach of a mammalian patient and reside therein, and being generally unable to pass through the pylorus while remaining within the bag 30. As used herein, the terms digestive-resistant and indigestible are intended to mean that the material used is not subject to the degrative effects of stomach acid and enzymes, or the general environment found within the gastric system over an extended period of time, therefore allowing the device to remain intact for the intended life of the device. However, this does not necessarily mean that the material cannot be degraded over time. One skilled in medical arts and gastrological devices would readily appreciate the range of materials that would be suitable for use as a long-term intragastric member.

The intragastric member may be formed from various materials. Many well-known plastics have suitable properties, including selected polyesters, polyurethanes, polyethylenes, polyamides, silicone, or other possible materials. Mammalian hair has been found to form natural bezoars, and thus, is also a possible material. However, some materials, such as certain polyamides, have been found to expand over time, which can be an undesirable property. Most other natural materials are generally relatively less resistant to acids and enzymes, and would therefore typically require treatment or combination with relatively more resistant materials to remain digestive-resistant in the gastric lumen over a relatively longer duration. Alternatively, the intragastric member may be formed from relatively less digestive-resistant materials for applications that require relatively short-term placement of the intragastric member in the gastric lumen.

In a preferred embodiment, the intragastric member comprises a digestive-resistant or indigestible member composed of a low density polyethylene. Fluorinated ethylene propylene, ethylene vinyl acetate copolymer, nylon, or types of polymers that are biocompatible and to which food will generally not adhere may also be utilized.

The intragastric member is available in a variety of sizes, shapes and diameters, which result in varying designs and configurations during advancement and placement in the stomach. As an example, FIG. 1 depicts a single intragastric member 11 in which the intragastric member 11 comprises a preformed expandable digestive-resistant member 12 having an elliptical shape. The intragastric member 11 includes a proximal end 13, a distal end 14 and a main body 15, wherein the proximal end 13 and the distal end 14 each provide an opening 16 to receive a securing mechanism.

Figure 2:
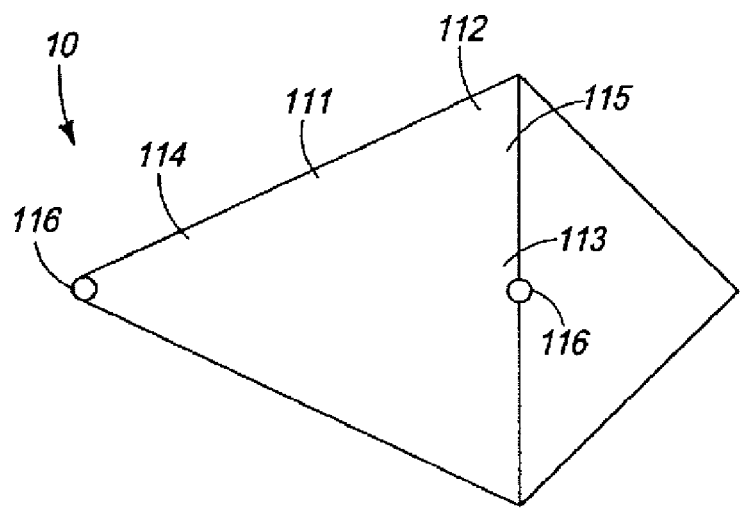
FIG. 2 depicts a pictorial view of another embodiment of an intragastric member of the present invention.

The intragastric member may also have the shape shown in FIG. 2. FIG. 2 depicts a single intragastric member 111 in which the intragastric member 111 comprises a preformed expandable digestive-resistant member 112 having triangular shaped faces. The intragastric member 111 includes a proximal end 113, a distal end 114 and a main body 115 which defines four faces. The intragastric member 111 also includes an opening 116 along the proximal end 113 and the distal end 114 to receive a securing mechanism. The main body 115 is modified or otherwise formed to include truncated edges to avoid ulcerating the stomach and to make the intragastric member 111 easier to deliver to the bag 30 (see FIG. 10) located in the gastric lumen. The triangular shaped faces may provide complimentary designs that engage each other within the bag 30 to displace relatively larger volumes in the gastric lumen. As will be explained in greater detail below, the bag 30 may further include an inner member (not shown) to seal the inner reservoir of the bag 30 after delivery of the intragastric member 111 into the bag 30. The bag 30 may be composed of a non-porous material, non-woven material, mesh material or other suitable material depending on the particular design.

Figure 3:
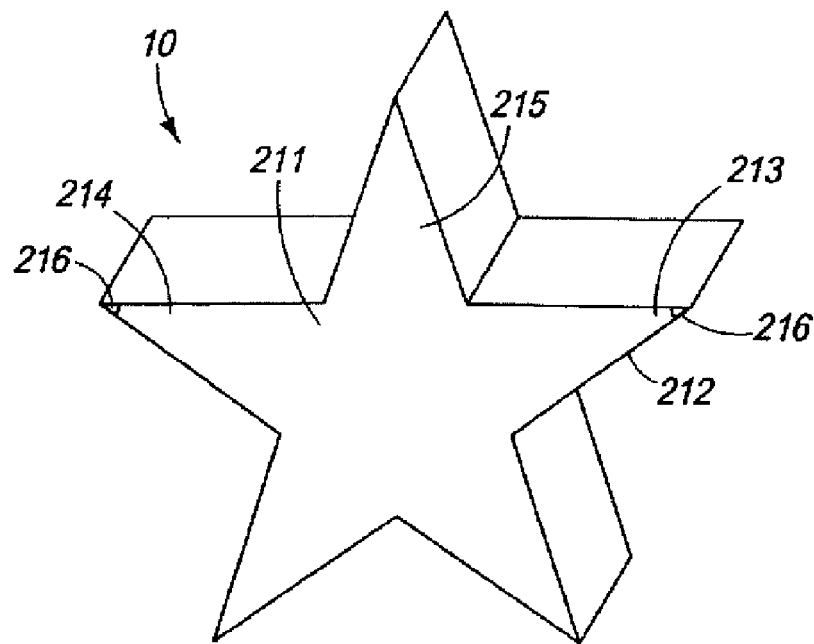
FIG. 3 depicts a pictorial view of another embodiment of an intragastric member of the present invention.

FIG. 3 depicts a single intragastric member 211 in which the intragastric member 211 comprises a preformed expandable digestive-resistant member 212 having a star-shape. The star-shaped intragastric member 211 includes a proximal end 213, a distal end 214 and a main body 215 which defines five protrusions. The intragastric member 211 also includes an opening 216 along the proximal end 213 and the distal end 214 to receive a securing mechanism.

Figure 4:
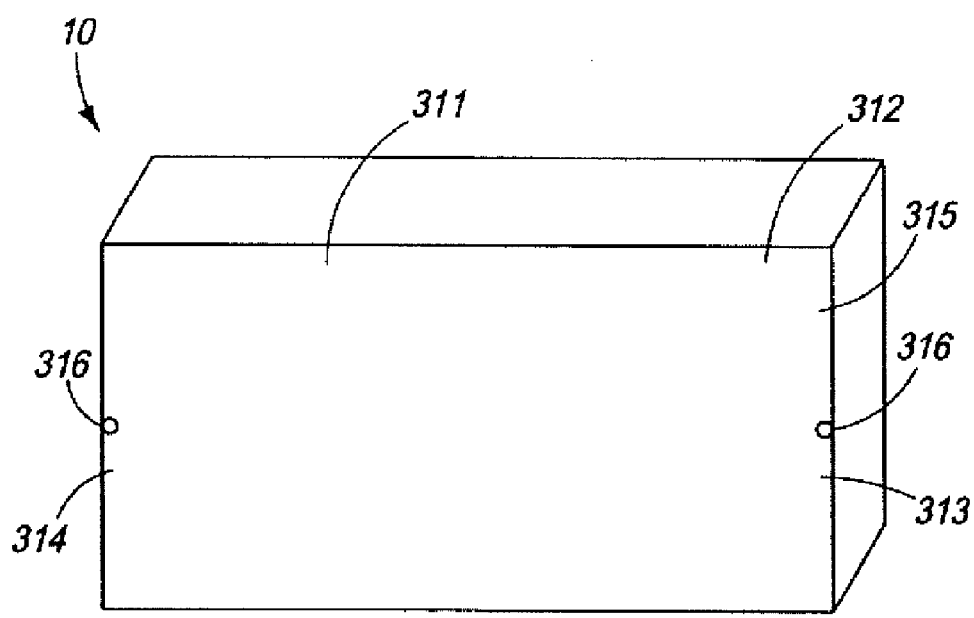
FIG. 4 depicts a pictorial view of another embodiment of an intragastric member of the present invention.

FIG. 4 depicts a single intragastric member 311 in which the intragastric member 311 comprises a preformed expandable digestive-resistant member 312 having a rectangular shape. The rectangular shaped intragastric member 311 includes a proximal end 313, a distal end 314 and a main body 315 which defines three pairs of opposing faces. The intragastric member 311 also includes an opening 316 along the proximal end 313 and the distal end 314 to receive a securing mechanism.

In an alternative embodiment (see FIG. 18), the intragastric members can include one or more strips of material that have been folded or gathered to form a series of elongated loops having a predetermined shape, such as disclosed in U.S. Pat. No. 7,066,945, the contents of which are hereby incorporated by reference.

Figure 20:
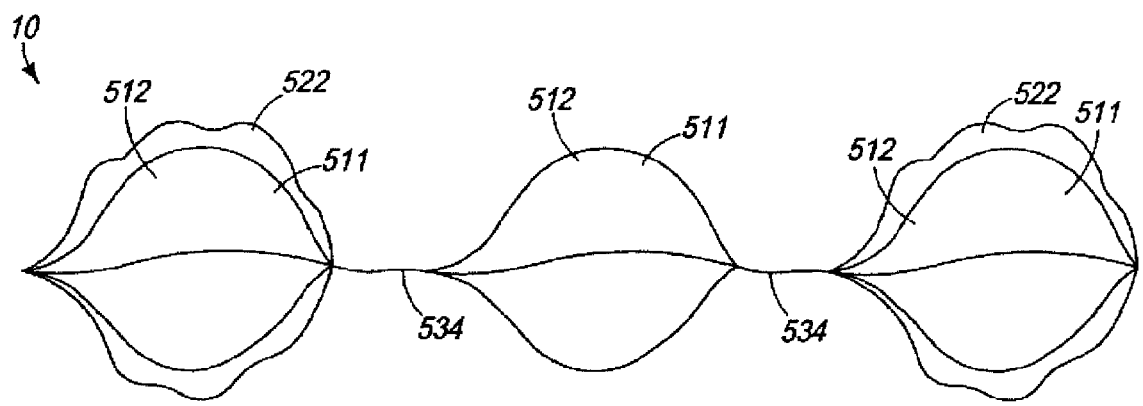
FIG. 20 depicts a pictorial view of another embodiment of an intragastric member of the present invention.

FIGS. 20-23 depict alternative embodiments of the intragastric member of the present invention. FIG. 20 depicts an intragastric member 511 wherein the intragastric member 511 comprises a chain of self-expandable wire-framed bulbs 512 coupled by a releasing mechanism 534. The bulbs 512 can further include a dissolvable coating 522 or splittable sheath to provide a protective layer to maintain the bulbs 512 in a compressed configuration during delivery and ingestion. Alternatively, the coating 522 may be configured to cover and enclose the wire frame structure. The bulbs 512 once expanded, apply pressure to the gastric lumen, thereby creating a feeling of fullness. The expanded bulbs 512 also displace volume within the stomach.

Figure 21:
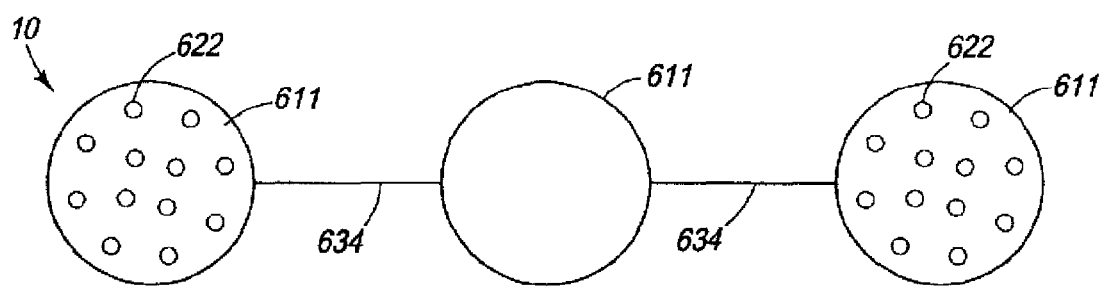
FIG. 21 depicts a pictorial view of another embodiment of an intragastric member of the present invention.

FIG. 21 depicts an alternative self-expandable intragastric member 611 comprising a spherical design coupled by a releasing mechanism 634. The intragastric member 611 further includes a hollow frame comprising a plurality of openings 622 along the surface. The openings 622 allow fluid of the gastric lumen to pass through the intragastric member 611 while also decreasing the overall mass of the intragastric member 611. Each of the intragastric members 511, 611 can be disposed within individual bags, or may collectively be disposed within a single bag.

Figure 22:
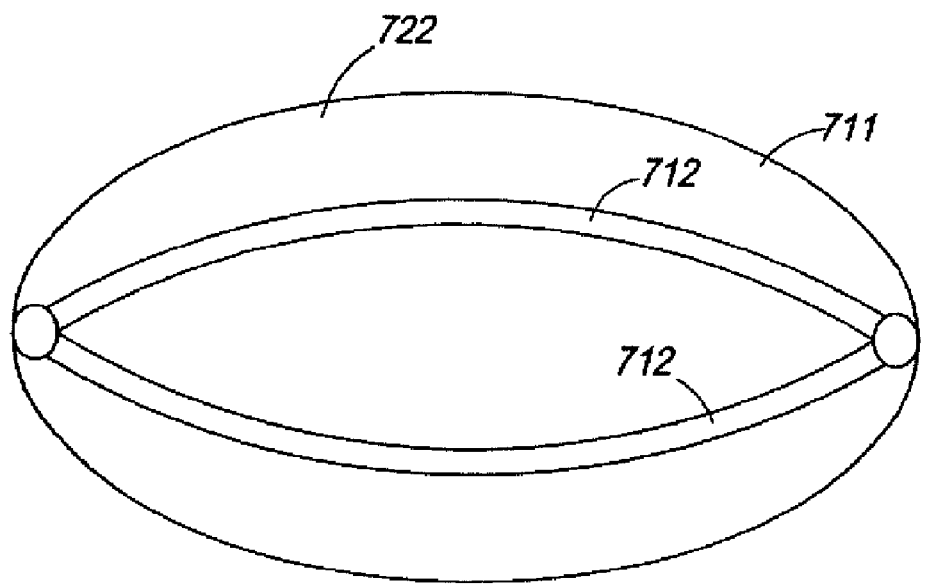
FIG. 22 depicts a pictorial view of another embodiment of an intragastric member of the present invention.

FIG. 22 depicts an intragastric member 711 comprising a nitinol cage 712 with a polymer coating 722 covering the nitinol cage 712. The nitinol cage 712 provides expandable ribs that are aligned longitudinally and bow outwardly upon delivery to the gastric lumen of a mammal to expand and maintain the polymer coating 722 in an expanded balloon-like configuration.

Figure 23:
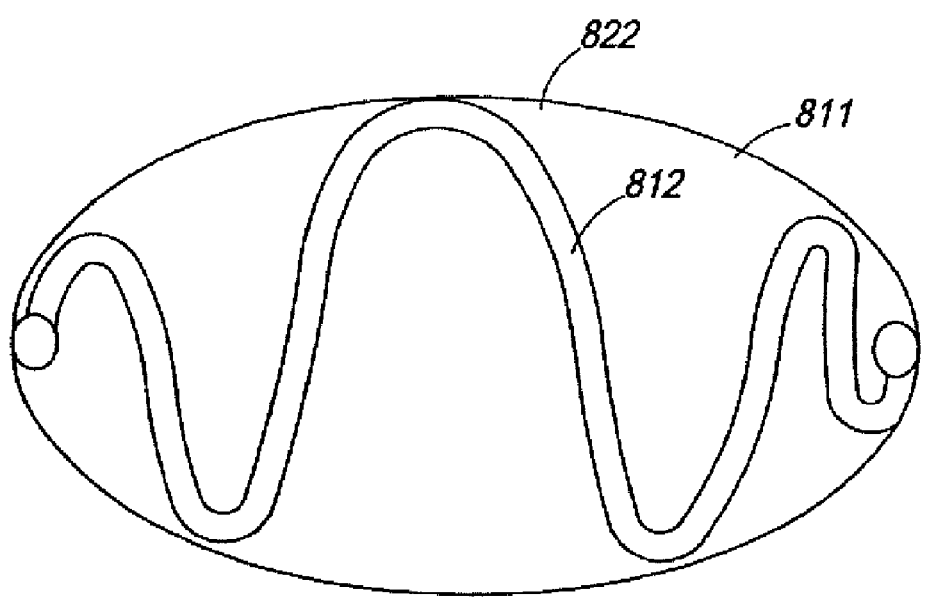
FIG. 23 depicts a pictorial view of another embodiment of an intragastric member of the present invention.

FIG. 23 depicts another self-expandable intragastric member 811 comprising a nitinol cage 812 with a polymer coating 822 covering the nitinol cage 812. The nitinol cage 812 includes expandable ribs that are aligned spirally that assume an expanded configuration upon delivery to the gastric lumen of a mammal.

The illustrative embodiments of intragastric members 511, 611, 711, 811 of FIGS. 20-23 can be delivered in a number of ways, depending on the size, number, and configuration of the devices, or according to the physician's preference. Likewise, the intragastric members 511, 611, 711, 811 can be joined together, or they can be delivered singly or in pairs, and grouped together after all the intragastric members 511, 611, 711, 811 have been placed within the bag 30. Additionally, the intragastric members can be delivered into a bag located in the gastric lumen of the patient in the same manner as will be described below in connection with FIGS. 10-12.

Figure 25:
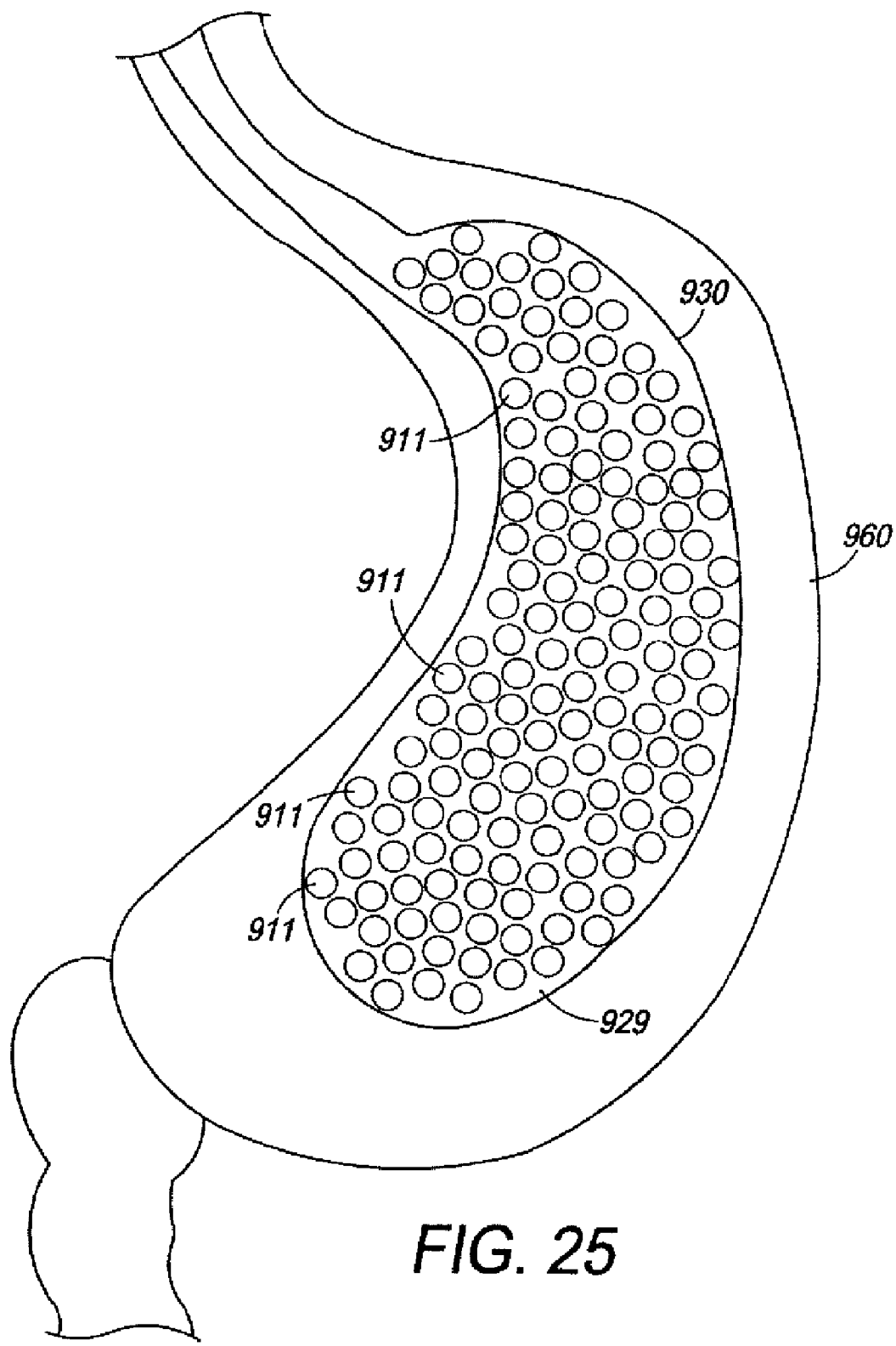
FIG. 25 depicts a pictorial view of another embodiment of a plurality of intragastric members after being delivered to a bag located in the gastric lumen.
Figure 26:
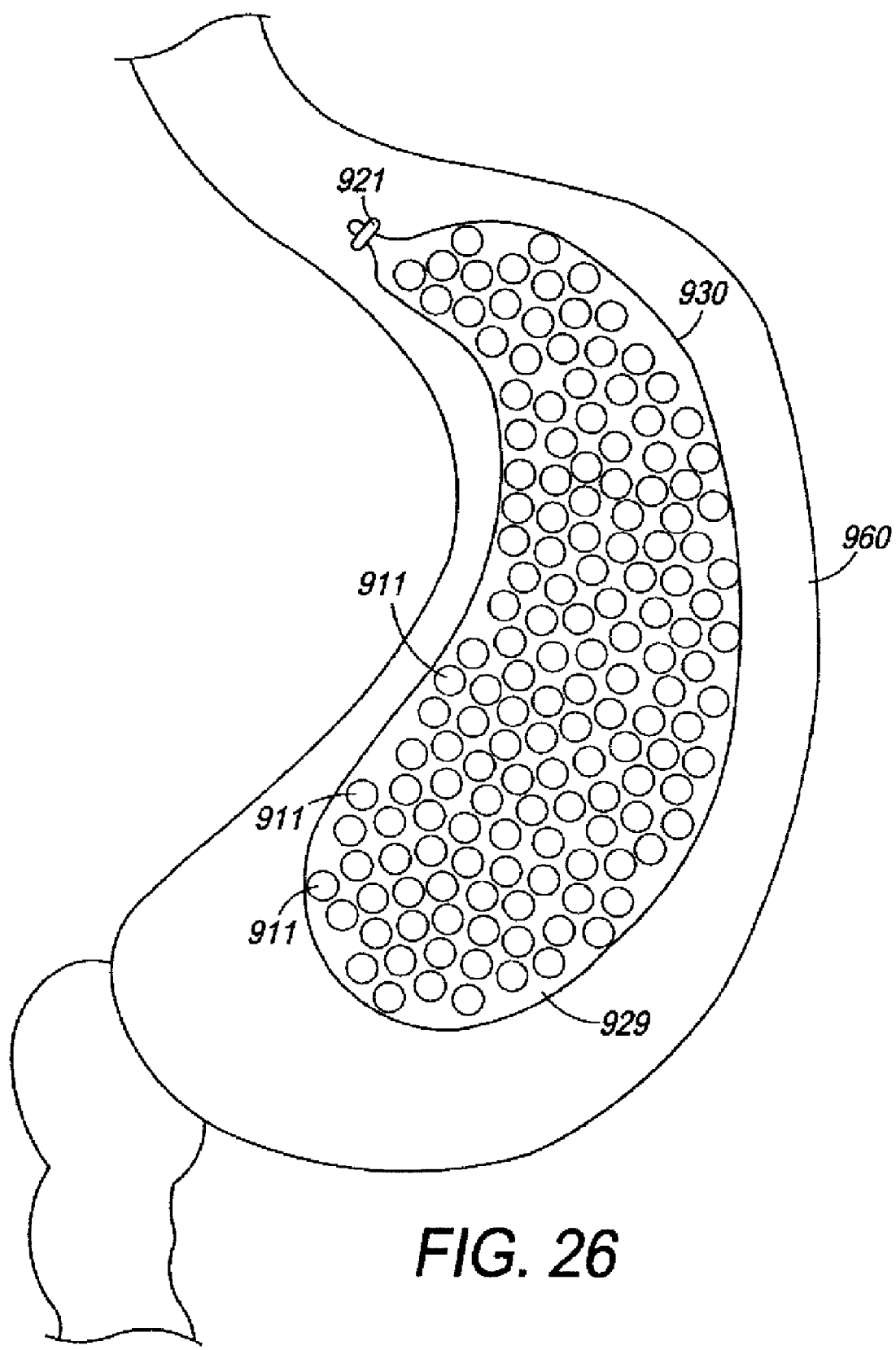
FIG. 26 depicts a pictorial view of a plurality of intragastric members of FIG. 25 secured with stopper after being delivered to the bag located in the gastric lumen.

FIGS. 25-26 depict yet another embodiment of the intragastric members wherein a plurality of intragastric members 911 are deployed into a bag 930 located in the stomach 960. The plurality of intragastric members 911 can comprise intragastric members 911 having varying sizes and shapes including structures such as beads, balls and the like. The intragastric members 911 may also comprise different material depending on the particular design. Additionally, varying numbers of the intragastric members 911 can be utilized to fill an inner member 929 of the bag 930 depending on the volume and shape of the bag 930. The intragastric members 911 can be inserted into the bag 930 separately or together to displace volume in the gastric lumen. The bag 930 may be secured by pushing a stopper 921 or similar constraining element along or about the opening of the bag 930.

As illustrated in FIGS. 1-4 and FIGS. 18-23, and FIGS. 25-26, varying shapes are contemplated to increase the amount of volume or space occupied by the corresponding intragastric member within the bag. Particularly, the varying shapes can provide a feeling of fullness upon engaging the lumen of the patient, i.e., the stomach walls of the patient. The varying shapes of the intragastric member further provide complimentary designs that engage each other to displace volume after placement into the bag 30 (see FIG. 10) in the gastric lumen of the patient. More specifically, and as will be explained is greater detail below, the shapes or combination of shapes are preferably selected to provide the bag 30 with an overall volume that is greater than the sum of the volumes of the individual intragastric members. It should be appreciated that other designs utilizing expandable or alterable shapes could also be utilized. For example, the intragastric members can be inflated or injected with saline or other suitable material to expand from a first configuration to a second configuration upon insertion into a bag. Alternatively, the intragastric members can comprise dissolvable material such as cellulose, gelatin, or some other dissolvable or rapidly degrading synthetic or biomaterial that dissolves upon contact with the fluid of the gastric lumen. Additionally, the intragastric member can be composed of an expandable material, a low density polyethylene or other suitable material. The intragastric member is not limited to one particular shape, but can comprise varying shapes depending on the particular use. The shapes of the constituent components can be selected from the group consisting of circular, round, elliptical, square, triangular, rectangular, pentagonal, hexagonal, star-shaped or any other suitable three dimensional shape.

Figure 5:
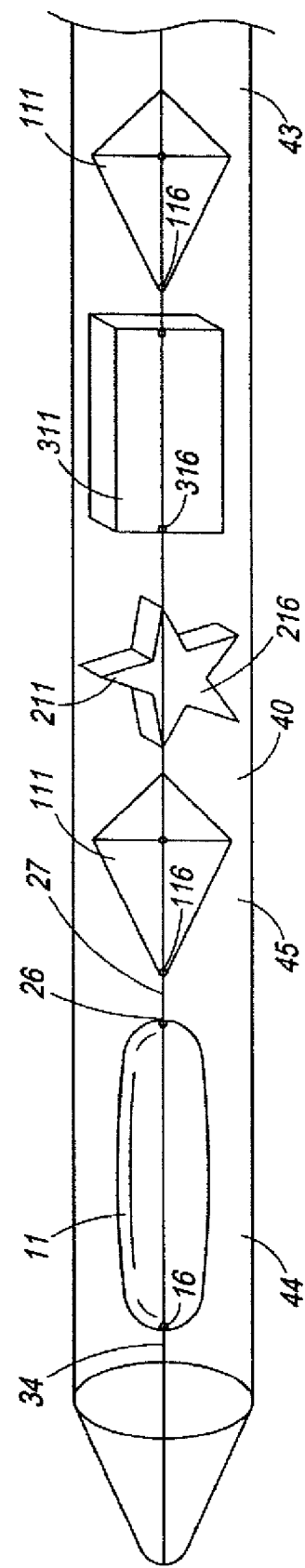
FIG. 5 depicts a plurality of intragastric members loaded onto a delivery tube for insertion into a bag located in the gastric lumen.

Results from human trials may lead to modifications in the configuration and structure of the intragastric members being depicted in the figures of this application. Nevertheless, it is already understood that the dimensions, shape, and construction of the intragastric member can be quite variable and still produce the desired results. For example, FIG. 5 depicts an embodiment of the present invention comprising intragastric members 11, 111, 211, 311 in which the respective preformed shapes include an ellipse, triangle, star and a rectangle. However, the invention can include alternative embodiments consisting of uniform shapes, such as a design consisting of only triangles, rectangles or other suitable preformed shapes. Other designs can include one or more preformed shapes comprising combinations of circles, squares or other suitable preformed shapes.

Various structures of the bag are contemplated. For example, the embodiment of the bag 430 depicted in FIGS. 18-19 can comprise a relatively impermeable material with a plurality of openings 422 positioned along the surface of the bag 430. The openings 422 allow fluid of the gastric lumen to pass through the bag 430 and be absorbed by the intragastric members 411. The fluids promote the dissolving of the outer package encasing the intragastric member 411, thereby allowing the intragastric member 411 to expand from a first configuration into a second configuration.

Figure 24:
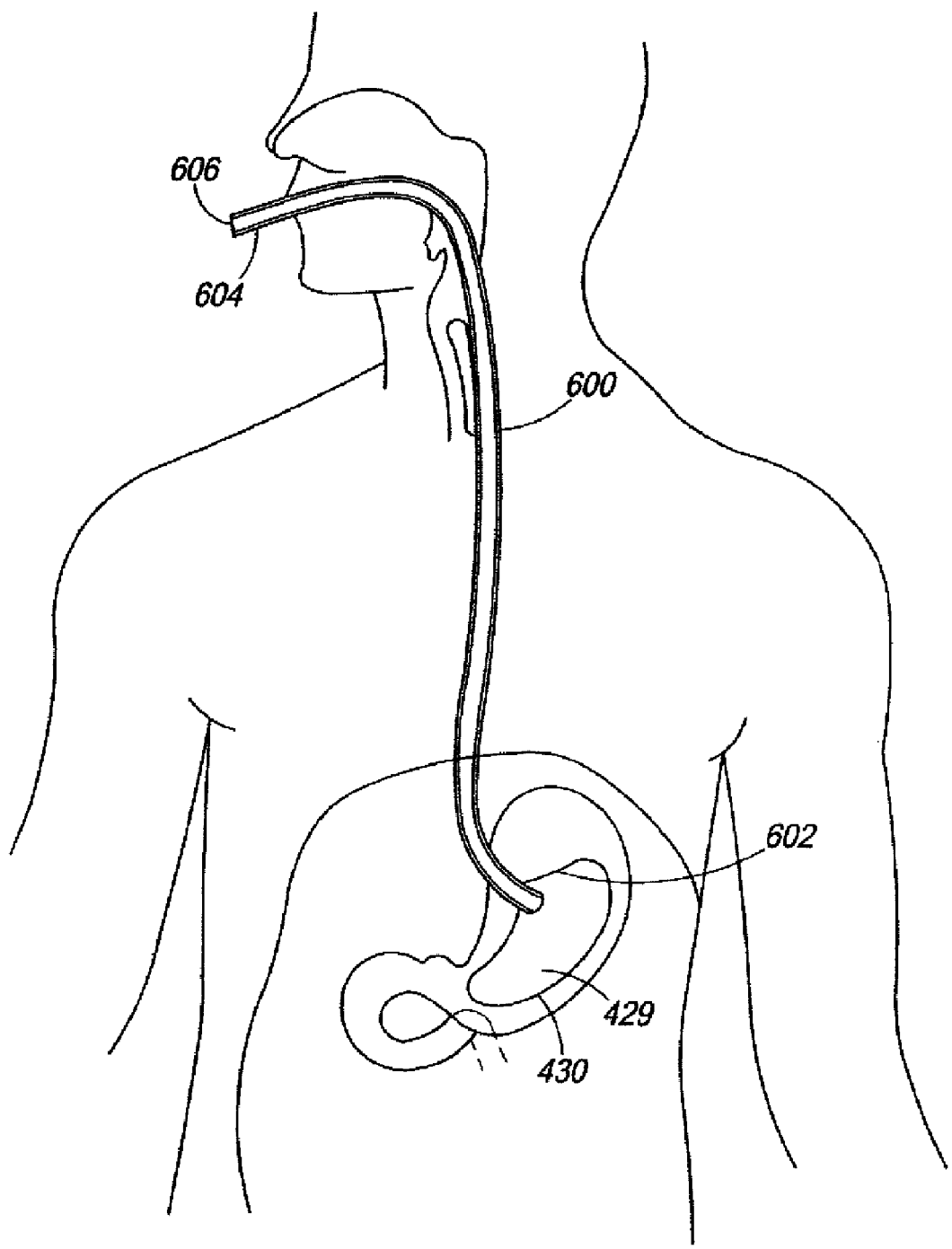
FIG. 24 depicts a partial, cross-sectional view showing a overtube positioned in the mouth and along the esophagus of a patient such that the overtube distal end is positioned in the gastric lumen of the stomach.

Having described various structures of the intragastric members and bag, delivery of the intragastric members and bag will now be discussed. FIG. 24 depicts an overtube 600 that is used to provide a passageway for delivering an intragastric member 11 to the bag 430 located in the gastric lumen of the patient. The overtube 600 may be used in combination with an endoscope to establish a passageway to a target delivery site in the stomach. Once the overtube 600 is positioned in the gastric lumen of the patient, the bag 430 is delivered to the stomach. The bag 430 is releasably coupled to the overtube 600, thereby allowing advancement of the bag 430 along the overtube 600 in a variety of ways. For example, the bag 430 can be delivered to the stomach utilizing a pusher member (not shown) to manually advance the bag through the overtube 600 and past the distal end of the overtube 600. Alternatively, the bag 430 may be delivered along the outside of the overtube 600. Upon delivery of the bag 430, the intragastric member 11 is passed through the overtube 600 to deliver the intragastric member 11 to the bag 430 located in the gastric lumen. Once the desired delivery in the gastric lumen is complete, the overtube 600 is removed. The bag 430 may also be delivered with a catheter based delivery system, or with a pair of medical forceps or any other suitable form of delivery.

The overtube 600 comprises a proximal end 604, a distal end 602 and a lumen 606. Any arrangement of the main lumen 606 is contemplated. The overtube 600 can have a single-piece construction as shown in the embodiment depicted in FIG. 24. Alternatively, several tubes may be bonded together to form the flexible overtube 600. The overtube 600 can be made from any suitable material known in the art including, but not limited to, polyethylene ether ketone (PEEK), polytetrafluorethylene (PTFE), polyamide, polyurethane, polyethylene and nylon, including multi-layer or single layer structures and may also include reinforcement wires, braid wires, coils and or filaments.

The lumen 606 is configured to receive and pass an intragastric member, or suitable secondary device, such as an endoscope. The lumen 606 ranges in size depending on the size of the intragastric member to be deployed. The size of the overtube 600 and corresponding intragastric member is provided for illustrative purposes only and are not intended to be construed as a limitation of the present invention. As one of ordinary skill in the art would appreciate, since the intragastric member and the endoscope and are advanced through the lumen 606, the size of the lumen 606 is related to the size of either the intragastric member or the endoscope, whichever is larger. One of ordinary skill in the art would also appreciate that the size of the intragastric member is related to the length, width, and material comprising the intragastric member. Thus, a flexible overtube 600 may have smaller or larger dimensions depending on the size of the intragastric member, endoscope or other secondary device used in conjunction with the overtube 600 and therefore any overtube 600 of varying dimensions is contemplated as being within the scope of the claims of the present invention.

The loading of the intragastric members into delivery devices will now be discussed. FIG. 5 depicts a delivery tube 40 providing a plurality of intragastric members 11, 111, 211, 311 of various shapes and designs that are loaded into the delivery tube 40. The delivery tube 40 includes a proximal end 43, a distal end 44 and a lumen 45. The intragastric members 11, 111, 211, 311 are loaded into the lumen 45 of the delivery tube 40 and secured by a retaining element 34, such as a nylon thread. The retaining element 34 can be elongated to serve as a coupling mechanism 26, such as a tether 27 (see also FIG. 9). The retaining element 34 feeds into the opening 16, 116, 216, 316 of each individual intragastric member 11, 111, 211, 311, which is loaded into the lumen 45 of the delivery tube 40, and extends to the proximal end 43 of the apparatus 10. The number of intragastric members 11, 111, 211, 311 may depend on how many intragastric members comprise a set or grouping (which will be discussed in greater detail below with respect to FIG. 9), the material used, and the length and the width of the delivery tube 40. The optimal length of the intragastric member may be determined by one of ordinary skill in the art considering these factors, as well by what is determined through experimentation to work best.

Figure 6:
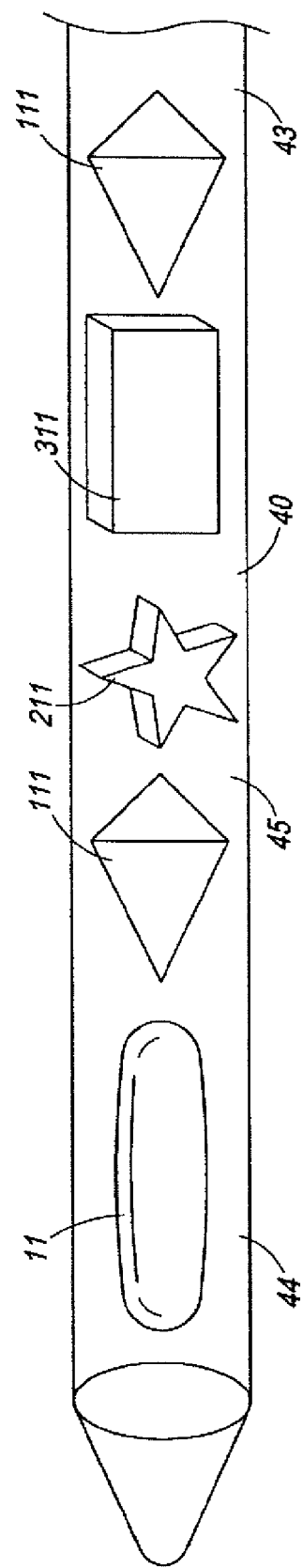
FIG. 6 depicts another embodiment of the plurality of intragastric members of FIG. 5 loaded onto a delivery tube for insertion into a bag located in the gastric lumen.

In the illustrative embodiments, the retaining element 34 (see FIG. 5) is located about the center of the delivery tube 40 to hold the intragastric members 11, 111, 211, 311 together. However, one of ordinary skill in the art would appreciate that other designs utilizing differently placed retaining elements 34, or eliminating them entirely, could also be utilized. For example, FIG. 6 depicts a plurality of intragastric members 11, 111, 211, 311 loaded into the lumen 45 of the delivery tube 40 wherein the distal end of each intragastric member 11, 111, 211, 311 is loaded behind the proximal end of each successive intragastric member 11, 111, 211, 311. The delivery system depicted in FIG. 6 does not include a retaining element 34. The intragastric members 11, 111, 211, 311 are preloaded onto the delivery tube 40 and then withdrawn therefrom by being pushed out with a pusher member (not shown) into the bag 30 (FIG. 10) that is located in the gastric lumen.

After loading the intragastric members into the delivery device, deployment can begin. The deployment of intragastric members can be accomplished in a number of ways, depending on the size, number, and configuration of the devices, or according to physician or patient preference. For example, the delivery tube 40 can be inserted and advanced through an overtube 600 of the type shown in FIG. 24. Once the distal end 44 is positioned inside the bag 30, (see FIG. 10), the intragastric members can be pushed or pulled out of the end thereof and into the bag 30 (e.g., with a pusher rod).

Figure 7:
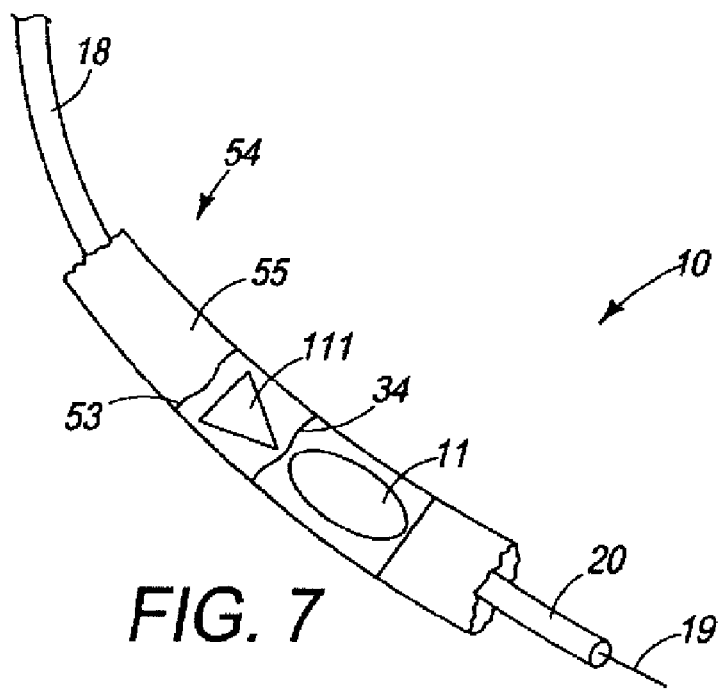
FIG. 7 depicts a pictorial view of a plurality of intragastric members with a delivery system.

FIG. 7 depicts an alternative delivery system 54 in which first and second intragastric members 11, 111 are mounted over a plastic overtube 18 and within a sheath 55. A series of suture ties 53, such as cotton thread, may constrain the first and second intragastric members 11, 111. As shown in the delivery system 54, the intragastric members 11, 111 are loaded over an overtube 18 by, for example, passing the overtube 18 through an opening in each of the intragastric members 11, 111. The intragastric members 11, 111 are secured by an outer sheath 55 made of a thin plastic material. In the illustrative embodiment, the suture ties 53 comprise a nylon thread or wire that is looped under and over the sheath 55, such that it can be withdrawn to tear through the thin material of the sheath 55 to release the intragastric member(s) 11, 111 mounted on the overtube 18. A releasing mechanism 20 feeds into a passageway 52 of the overtube 18, where it extends to the proximal end of the apparatus 10. Other types of splittable sheaths 55 can also be used, such as the COOK® PEEL-AWAY Introducer Sheath from Cook Inc., Bloomington, Ind. A wire guide 19 is typically used in the procedure, and is placed through the passageway of the overtube 18 to guide the distal end of the delivery system 54 to the gastric lumen of the patient.

Figure 8:
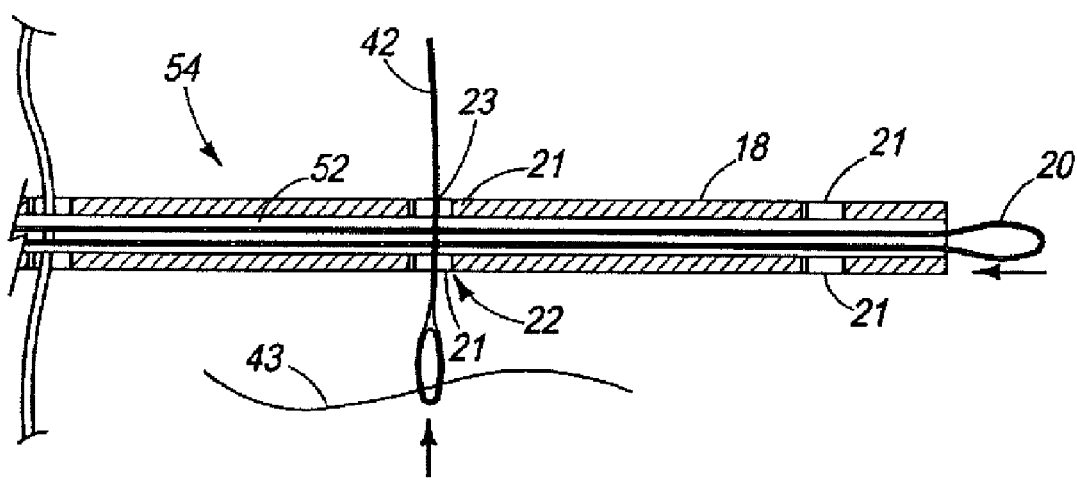
FIG. 8 depicts a sectional view of a plurality of intragastric members with a delivery system.

As shown in FIG. 8, the overtube 18 includes a plurality of apertures 21, a pair of which (e.g., apertures 22 and 23) are spaced apart a predetermined distance. Preferably, the apertures 22 and 23 are spaced apart approximately 2 cm along the distal portion of the overtube 18. The apertures 22 and 23 may also be spaced apart by other distances. To secure the intragastric members 11, 111 to the overtube 18, the suture tie 53 is pulled through the first aperture 22 using a device 42 such as a loop, hook, snare, etc. It is fed through the releasing mechanism 20, such as the illustrative wire loop, and then pulled through the opposite aperture 23. The intragastric members 11, 111 are then placed on the overtube 18, and the suture ties 53 are secured, thereby constraining the intragastric members 11, 111 into a first configuration for delivery. Once the distal end of the delivery system 54 has been introduced into the bag 30 (see FIG. 10) located in the gastric lumen, the releasing mechanism 20 is pulled back through the overtube 18, thereby severing the suture ties 53 one by one and releasing the intragastric members 11, 111 into the bag 30 where they can assume a second configuration that is sufficiently voluminous such that the bag 30 cannot pass from the stomach.

Figure 9:
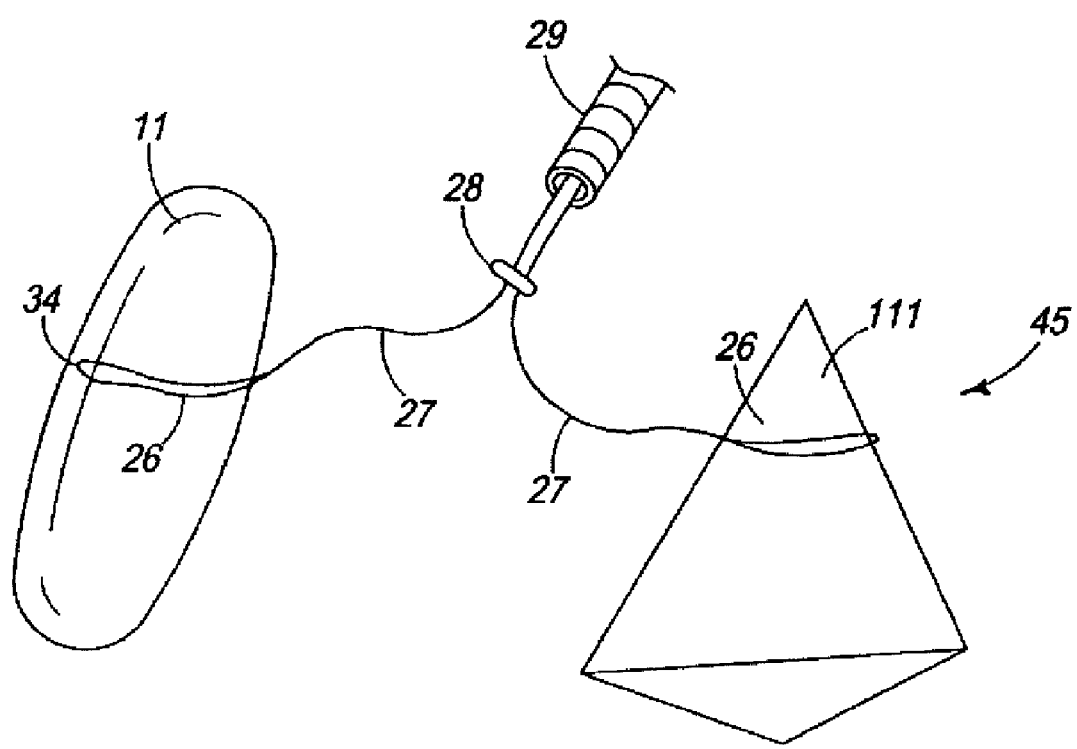
FIG. 9 depicts a pictorial view of a plurality of intragastric members with a delivery system.

After deployment of the apparatus 10, in order to create an obesity treatment apparatus 10 that will be retained in the stomach, it may be necessary to couple the intragastric members 11, 111 together to form a grouping or set 45 of intragastric members. The grouping or set 45 of intragastric members is sized such that it becomes sufficiently too large to pass through the pylorus. As an example, FIG. 9 shows two deployed intragastric members 11, 111 that each have a coupling mechanism 26 (i.e., tether 27) attached about them such that they can be drawn together. A pusher member 29, such as a catheter or corrugated metal tube, may be advanced into the gastric lumen through the working channel of an endoscope (not shown), and is guided over the tethers 27 to urge a securing element 28, such as a rubber patch, tightly against the two intragastric members 11, 111. The tethers 27 can then be cut from the pusher member 29, thereby allowing the grouping 45 to float unconstrained within the bag 30 that is disposed in the gastric lumen. The grouping 45 is too large to pass through the pylorus. This method can also be used to join additional intragastric members 11, 111 to form a larger grouping 45, if desired.

Likewise, the illustrative delivery system 54 of FIG. 8 can be used to deliver any practical number of intragastric members 11, 111 which can then be grouped in the manner described above in FIG. 9. Alternatively, the intragastric members 11, 111 may be delivered singly or in pairs, and then grouped together after all of the intragastric members 11, 111 have been placed in the bag 30.

Figure 10:
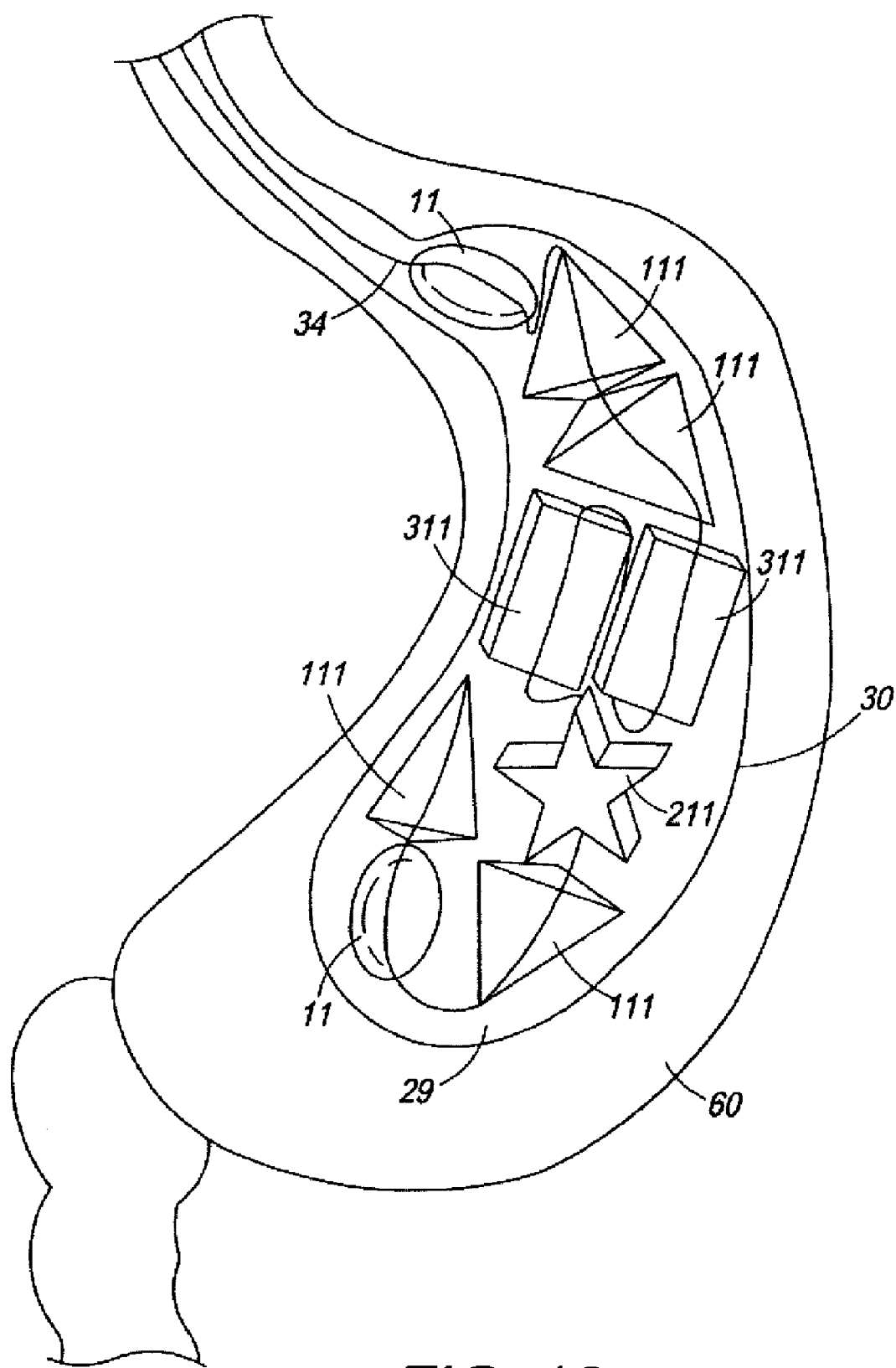
FIG. 10 depicts a pictorial view of a plurality of intragastric members of FIG. 5 coupled with nylon thread after being delivered to the bag located in the gastric lumen.
Figure 11:
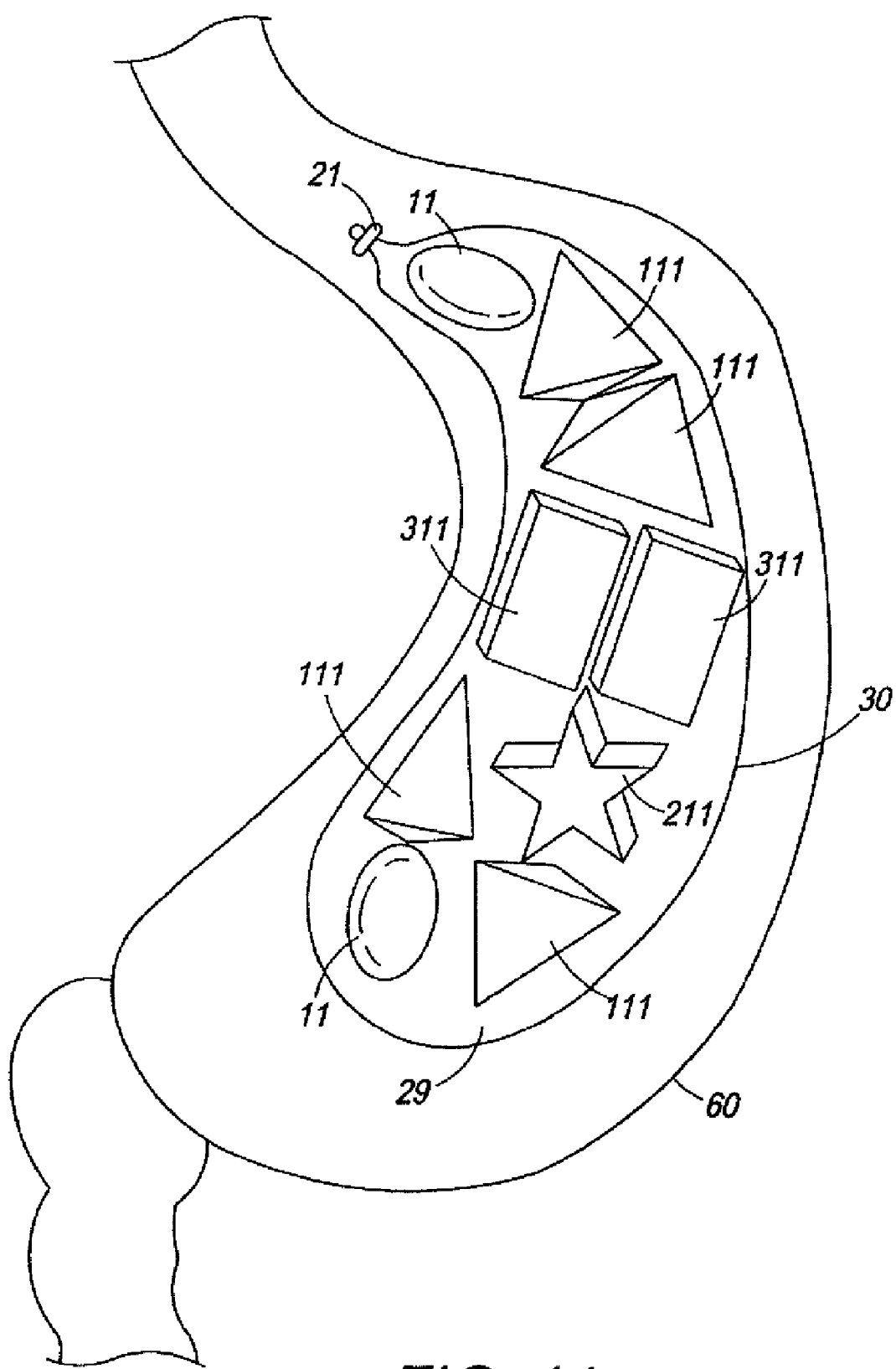
FIG. 11 depicts a pictorial view of a plurality of intragastric members of FIG. 10 secured with stopper after being delivered to the bag located in the gastric lumen.
Figure 12:
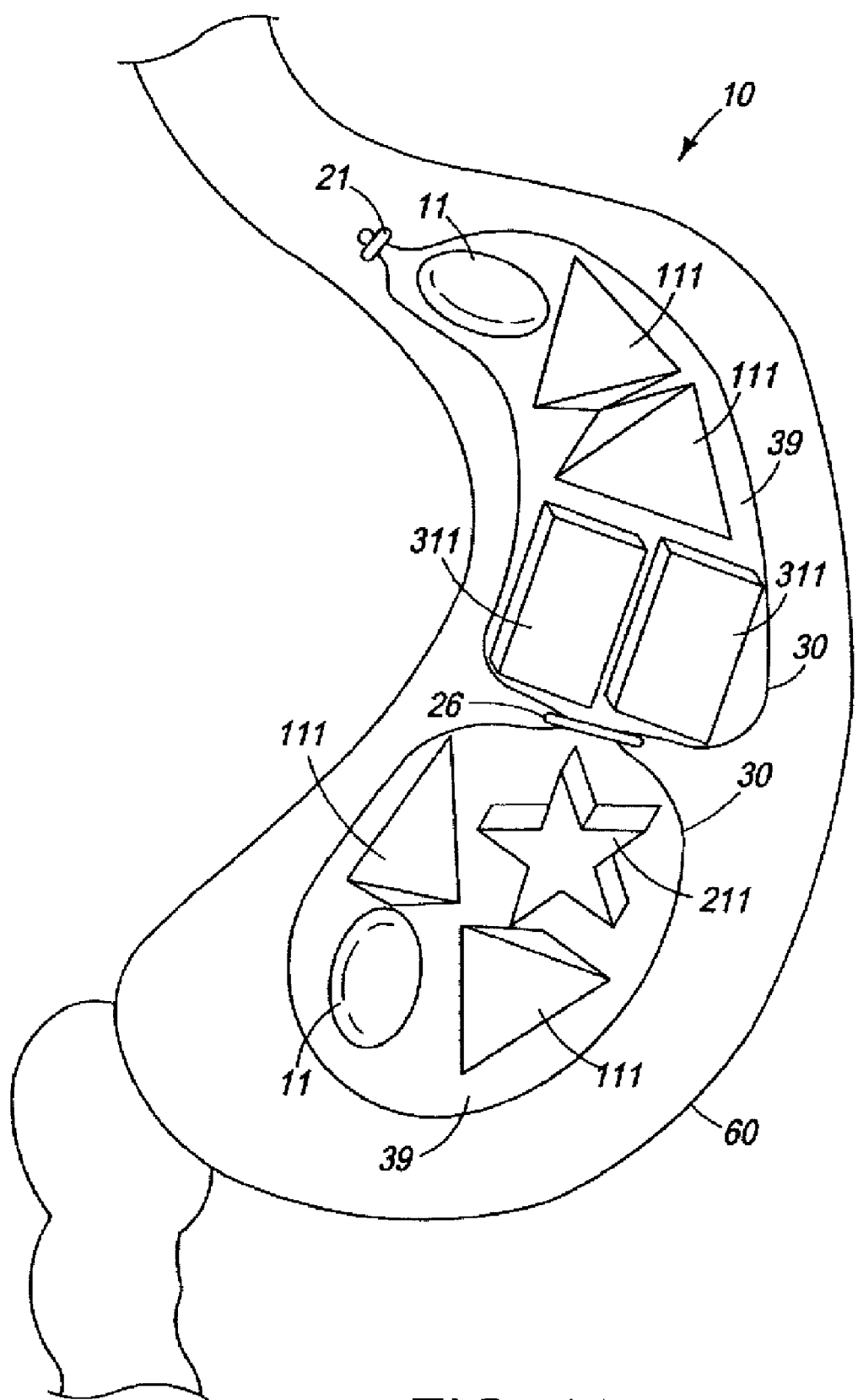
FIG. 12 depicts a pictorial view of a plurality of intragastric members of FIG. 11 secured with coupling mechanism after being delivered to the bag located in the gastric lumen.

FIGS. 10-12 depict a plurality of intragastric members 11, 111, 211, 311 that have been deployed into a bag 30 located in the gastric lumen. FIG. 10 shows the intragastric members 11, 111, 211, 311 deployed into the bag 30 after being transferred from a delivery device (e.g., delivery tube 40 of FIG. 5) in which the members 11, 111, 211, 311 were secured by retaining element 34. After the intragastric members 11, 111, 211, 311 are deployed into the bag 30, the retaining element 34 may be removed, as shown in FIG. 11. Additionally, in order to enclose the bag and prevent the intragastric members 11, 111, 211, 311 from inadvertently falling out of the bag 30, the bag 30 is preferably secured with a stopper 21 (FIG. 11).

Although the intragastric members 11, 111, 211, 311 are sufficiently small such that they can be introduced into the bag 30 of the gastric lumen as a set, the adherence of mucous and other changes that occur within the stomach 60 environment can, over time, significantly increase the volume of the filled bag 30 such that it becomes difficult to remove the intragastric members 11, 111, 211, 311 from the stomach 60. To address this problem, as depicted in FIG. 12, the intragastric members 11, 111, 211, 311 can be separated into two or more groupings 39 within the bag 30 by a coupling mechanism 26. The multiple groupings 39 may be cut apart when it is time to remove the intragastric members 11, 111, 211, 311 from the patient.

Figure 13:
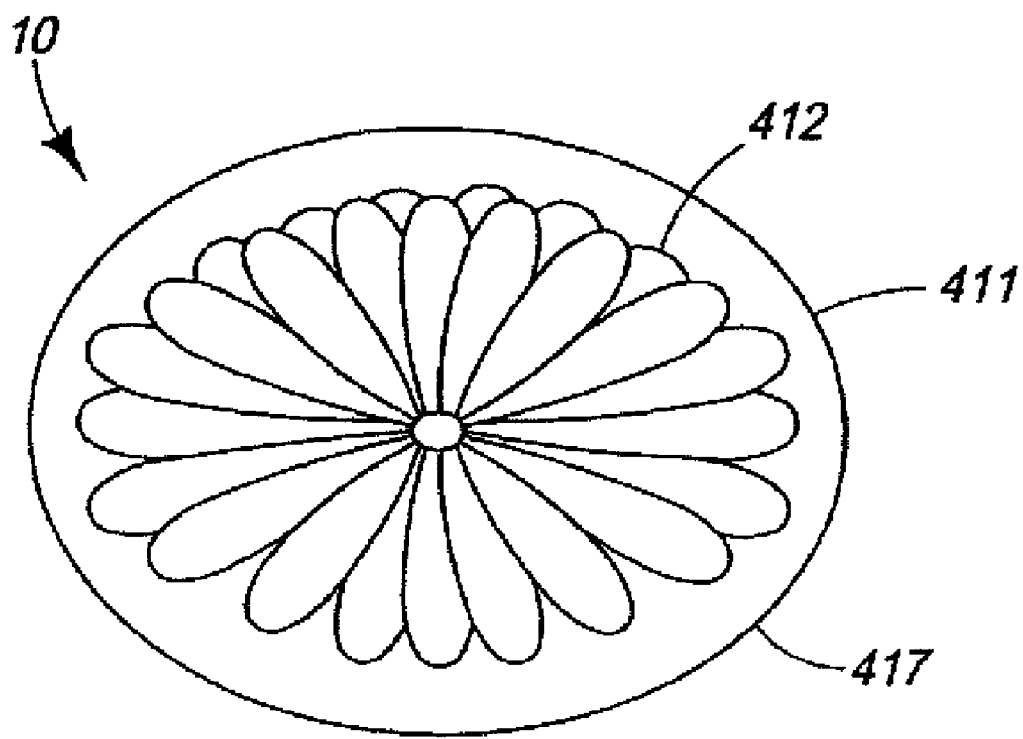
FIG. 13 depicts a pictorial view of another embodiment of an intragastric member of the present invention encased in a dissolvable outer package.

FIG. 13 depicts yet another embodiment of an intragastric member 411 of the present invention. In this embodiment, the intragastric member 411 comprises a material, such as nylon thread or a strip of nylon material, that has been tied into a nylon ball 412 or bundle and includes an outer member comprising a dissolvable enclosure 417. FIG. 13 shows that the dissolvable enclosure 417 constrains the intragastric member 411 in the first configuration. The dissolvable enclosure 417 comprises a material, such as cellulose, gelatin, glycerin, or some other dissolvable or rapidly degrading synthetic or biomaterial material, that allows the intragastric member 411 to be deployed in the first configuration into a bag 430 located in the stomach 460. Once the outer enclosure 417 has dissolved or degraded away, the intragastric member 411 expands from the first configuration into the second configuration (see, e.g., FIG. 16). The nylon ball 412 can be inserted into the bag 430 separately or coupled together with additional nylon balls 412 to displace an increased volume in the gastric lumen. The embodiment of FIG. 13 can be delivered with or without a catheter-based delivery system 54 (e.g., delivery tube 40 of FIG. 5), or swallowed by the patient, depending on the outer dimensions of the apparatus 10. The material comprising the intragastric member 411 is not limited to nylon and can include other material such as high-density polyethylene, or other suitable material.

Figure 14:
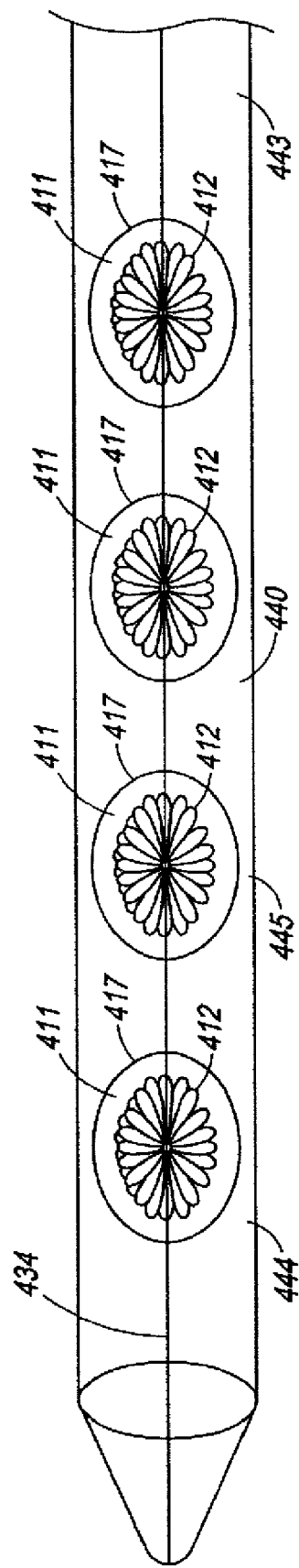
FIG. 14 depicts a plurality of intragastric members of FIG. 13 loaded onto a delivery tube for insertion into a bag located in the gastric lumen.
Figure 15:
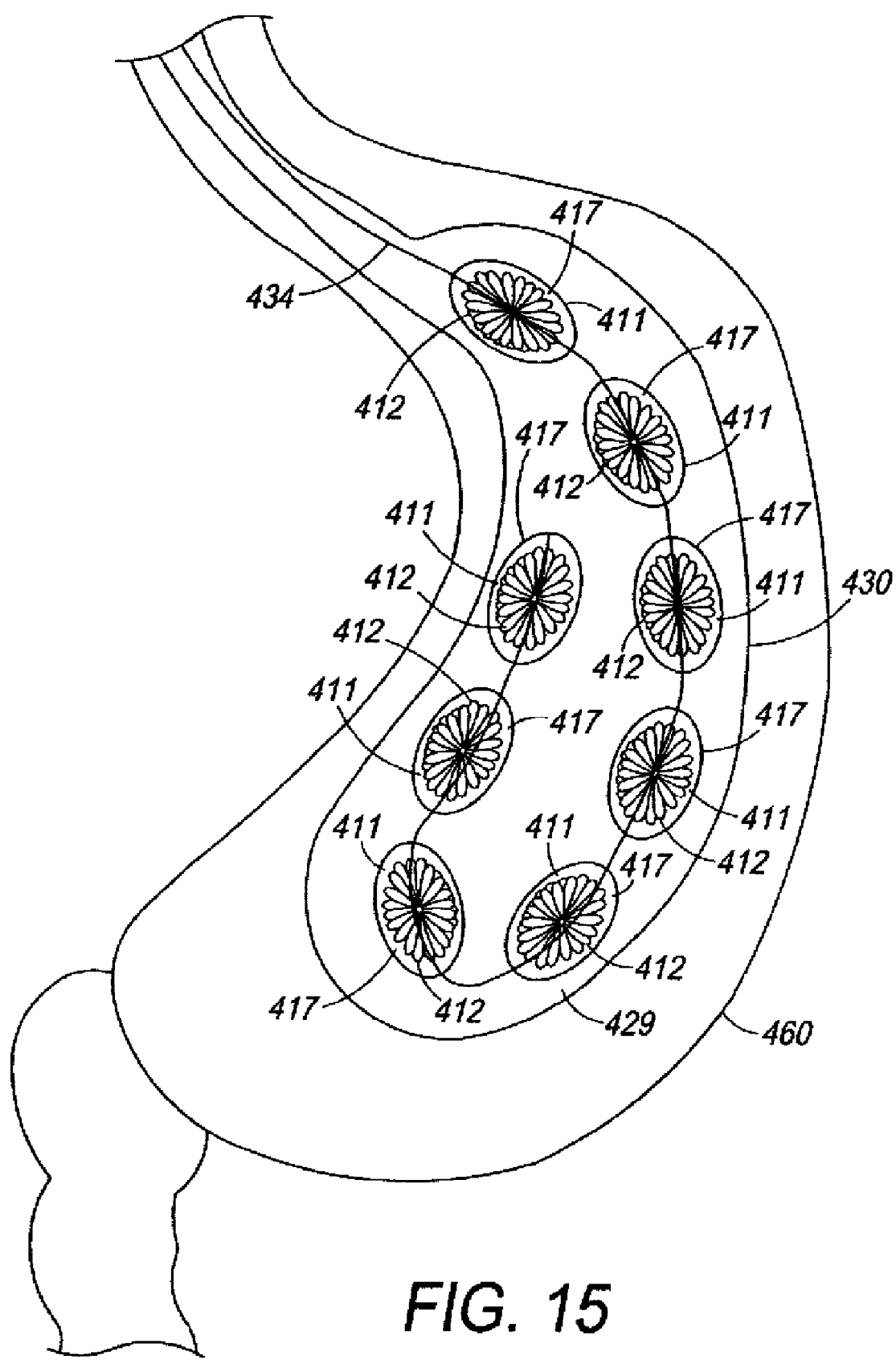
FIG. 15 depicts a pictorial view of a plurality of intragastric members of FIG. 14 coupled with nylon thread after being delivered to the bag located in the gastric lumen.
Figure 16:
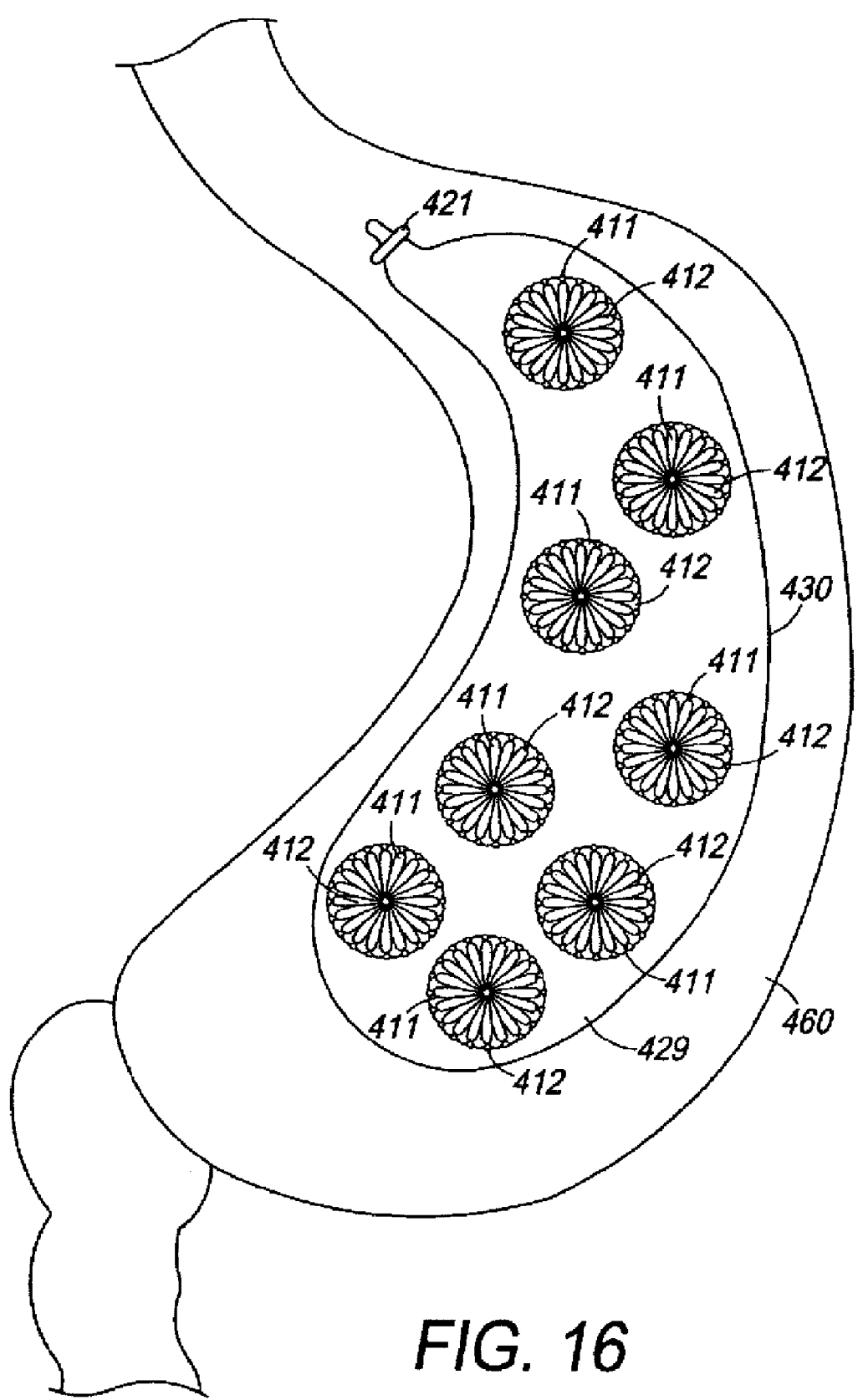
FIG. 16 depicts a pictorial view of a plurality of intragastric members of FIG. 15 secured with stopper after being delivered to the bag located in the gastric lumen.

FIG. 14 depicts a plurality of intragastric members 411 configured for delivery into the bag 430 located in the gastric lumen. FIGS. 15 and 16 depict successive steps of delivering the intragastric members 411 into the bag 430. During delivery of the intragastric members 411, a distal end 444 of a delivery tube 440 is positioned in the gastric lumen. Each intragastric member 411 is then manually pushed in a distal direction with a pusher member (not shown). The pusher member is inserted into a proximal end 443 of the delivery tube 440 and slid towards the distal end 444 of the delivery tube 440 so as to push the intragastric member 411 past the distal end 444 of the delivery tube 440 (see FIG. 14) and into the bag 430 (FIG. 15).

This procedure is repeated until all of the intragastric members 411 have been inserted into the bag 430 located in the stomach 460 (see FIG. 15). The bag 430 is then secured by removing the retaining element 434 from the intragastric members 411 and pushing a stopper 421 or similar device (see FIG. 16) along the opening of the bag 430 so as to enclose the intragastric members 411 within the bag 430. The delivery tube 440 is then withdrawn so as to leave the intragastric members secured in the bag 430. As illustrated in FIG. 16, the outer enclosure 417 is then allowed to dissolve, thereby allowing the intragastric members 411 to expand to the second configuration and substantially fill the bag 430. The expansion of the intragastric members 411 causes the overall volume of the bag 430 to increase and thereby displace volume of the gastric lumen.

Figure 17:
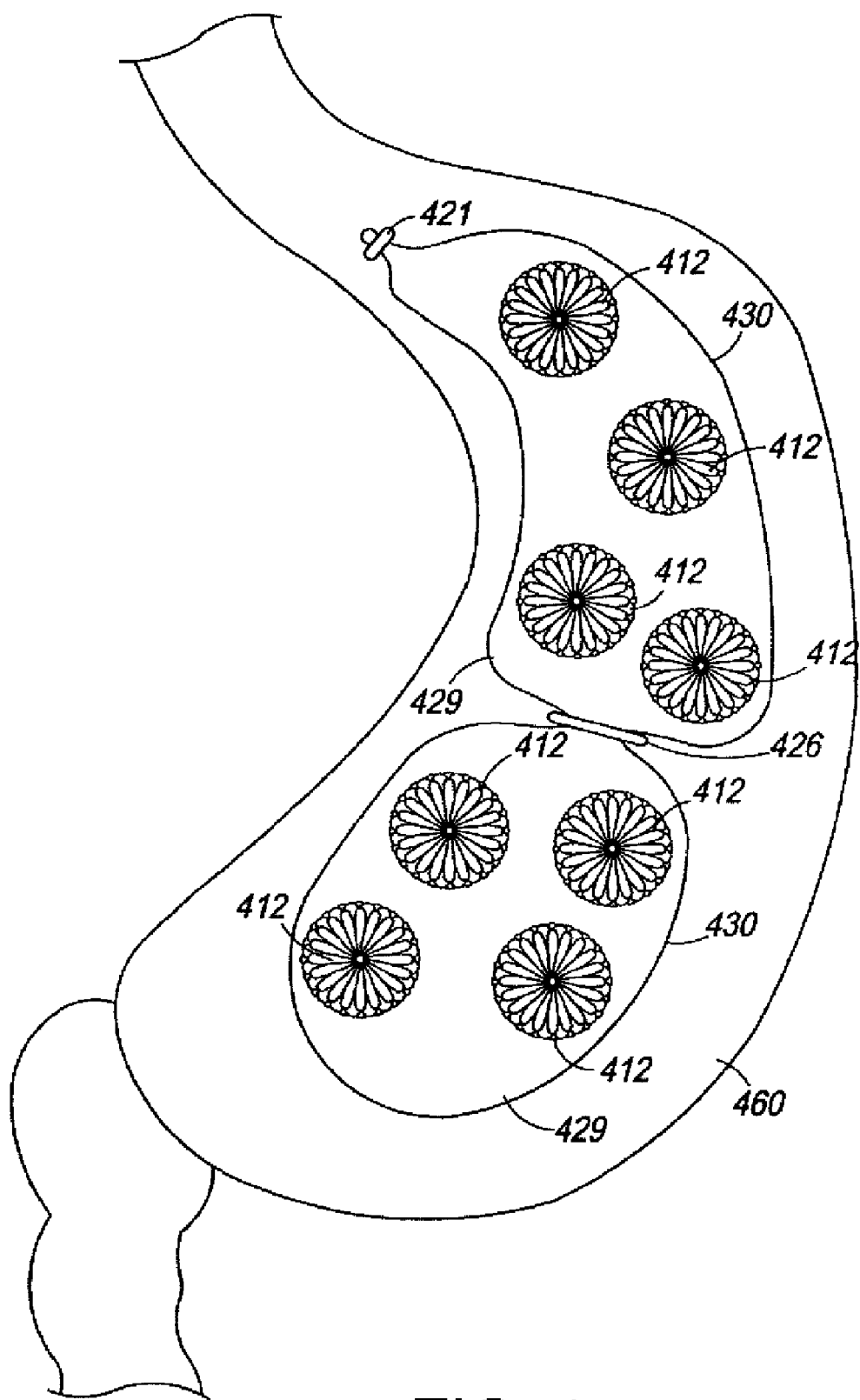
FIG. 17 depicts a pictorial view of a plurality of intragastric members of FIG. 16 secured with coupling mechanism after being delivered to the bag located in the gastric lumen.
Figure 18:
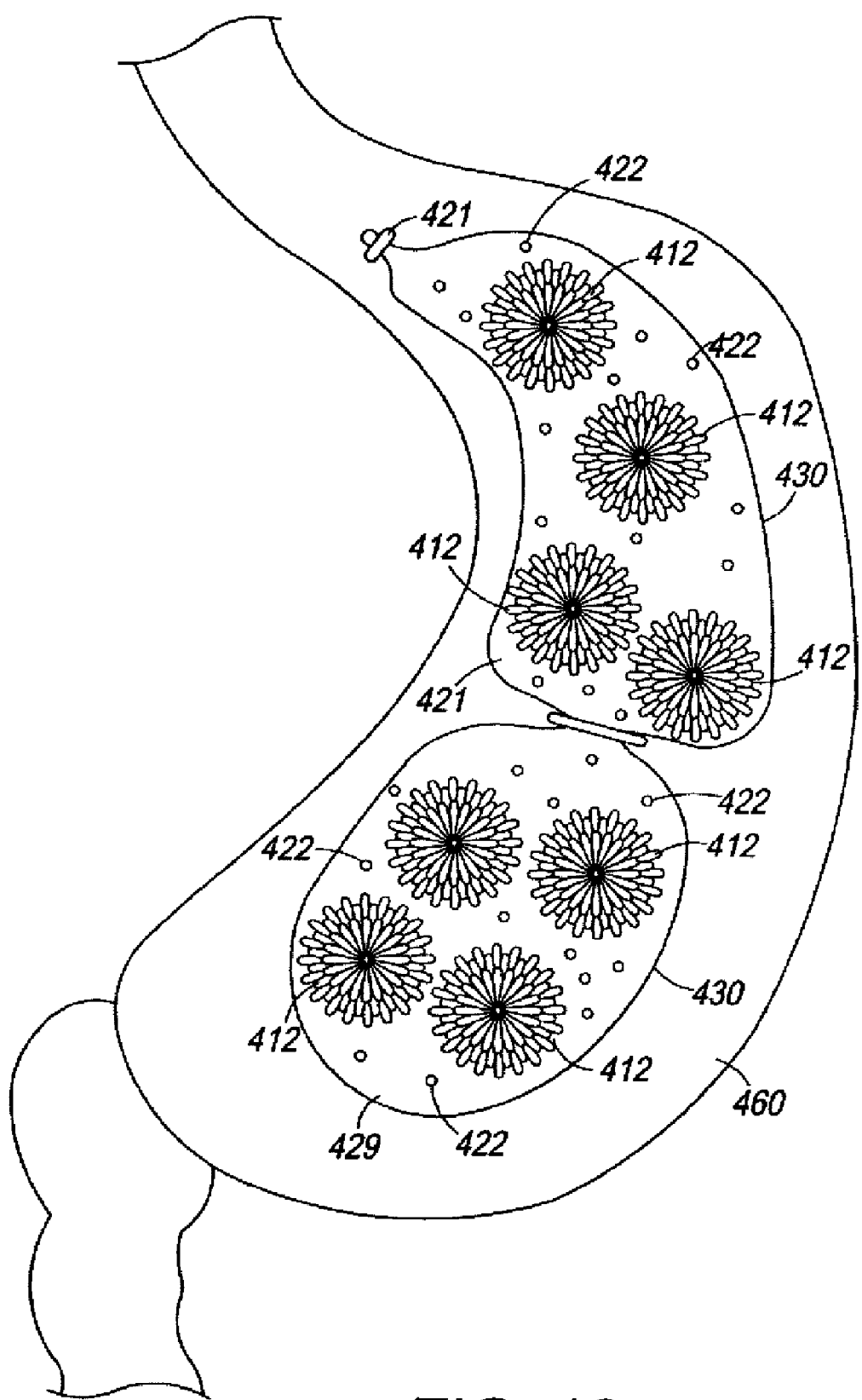
FIG. 18 depicts a pictorial view of a bag of the present invention having a plurality of openings located along the surface of the bag located in the gastric lumen.
Figure 19:
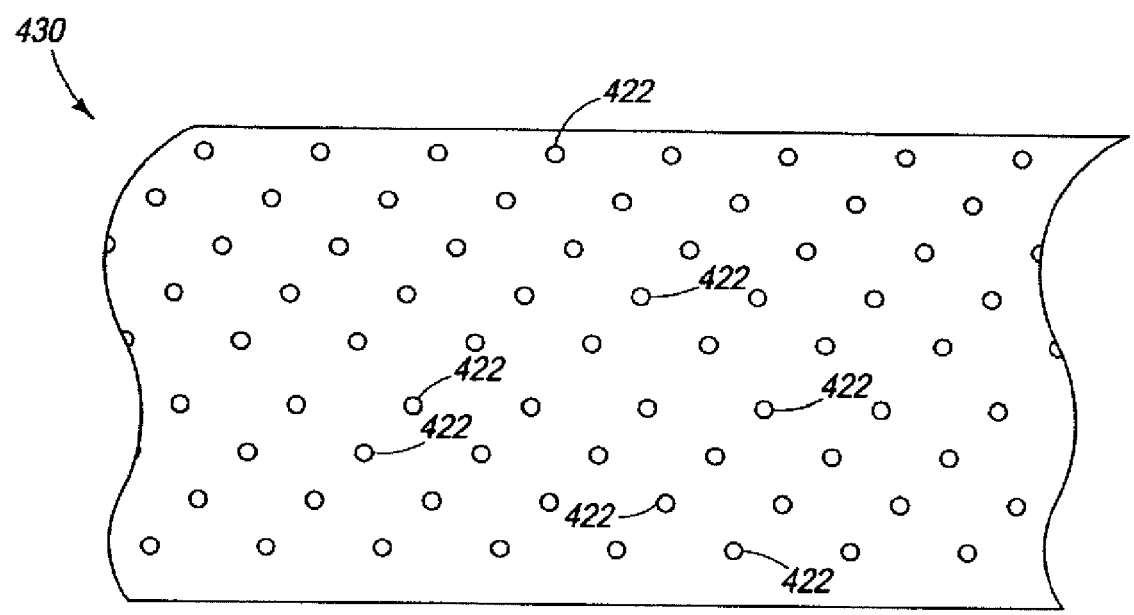
FIG. 19 depicts a sectional view of the bag of FIG. 18 having a plurality of openings located along the surface of the bag located in the gastric lumen.

Although the arrangement or grouping of intragastric members 411 shown in FIG. 16 is sufficiently small such that it can be introduced into the bag 430 of the gastric lumen as a set, the adherence of mucous and other changes that occur within the stomach 460 environment can, over time, significantly increase the volume of the apparatus 10. The increased size can make it very difficult to remove the grouping from the stomach 460. To address this problem, multiple intragastric members 411 are grouped together by a coupling element after introduction into the bag 430 and then cut apart when it is time to remove them from the patient. By severing the coupling element, the individual intragastric members of the grouping can be removed one at a time by using an endoscope and retrieval device. A coupling mechanism 426, such as a nylon thread, can be tied or otherwise secured to the filled bag 430 of FIG. 16 so as to form separate groupings of intragastric members 411 as shown in FIG. 17. The coupling mechanism 426 comprises nylon thread (e.g., standard nylon fishing line), that is wrapped around the grouping of intragastric members 411 to pull them into close contact with one another. The grouping is released by severing the line comprising the coupling mechanism 426 and the intragastric members 411 are removed one at time using a retrieval device such.

As illustrated in FIGS. 14-17, the bag 430 includes any shape suitable to receive an intragastric member thereby increasing the amount of volume or space occupied in the gastric lumen. Particularly, the structure and shape of the bag 430 includes any shape that provides a feeling of fullness upon engaging the stomach walls of the patient, such as an oval, circle, triangle, square and rectangle. The varying shapes of the bag 430 further provide complimentary designs to properly receive the varying shapes of the intragastric member after placement into the bag 430. The bag 430 may further include an inner member 429 to seal the inner reservoir of the bag 430 after delivery of the intragastric member into the bag 430. In the embodiments illustrated, the bag 430 can comprise suitable materials which include polytetraflouroethylene (PTFE), polyethylene terephthalate, polyester, polyurethane, silicone, Dacron, Thoralon, polypropylene knit, and other material which will be apparent to those of skill in the art in view of the present invention. Alternatively, the bag 430 can comprise degradable materials having coatings comprising indigestible polymers and the like. The bag 430 is not limited to a mesh design and can include alternative embodiments consisting of gastric socks, balls or similar devices.

In another embodiment of the present invention, the apparatus 10 can comprise one or more bags to receive the intragastric members 411. The bags can include varying configurations and shapes to receive the intragastric members. For example, a pair of bags can be connected in a concentric configuration, wherein the pair of bags share a common axis. The bags may also include varying properties, such as a first bag having a porous membrane allowing fluid from the gastric lumen to pass therethrough, and a second bag having a non-porous membrane preventing the passage of any gastric fluids therethrough. The bags may also comprise either a resilient elastomeric material or a substantially non-compliant material. Bags comprising the resilient elastomeric material include the ability to stretch when filled with the intragastric members 411. Conversely, bags comprising the substantially non-compliant material include the ability to form a predetermined final shape and volume when filled with the intragastric members 411.

The bag can be delivered a number of ways, depending on the size and configuration of the intragastric members. For example, one delivery system depicted in FIGS. 25-26 utilizes an elastic band (not shown) attached to the opening of the bag 930 which is inserted over an overtube 600 (FIG. 24) wherein the remainder of the bag 930 is inverted into the lumen of the overtube. As illustrated in an embodiment depicted in FIG. 25, upon delivery into the bag 930, the intragastric members 911 are subsequently pushed into the bag 930 until the bag 930 is filled. Additionally, a coaxial outer tube or similar device can be utilized to remove the elastic band from the overtube and thereby secure the bag 930 with the elastic band. The elastic band is configured to elastically retract around the opening of the bag 930 after being removed from the overtube to secure the intragastric members 911 within the bag 930. This delivery system can be utilized to delivery intragastric members of various configurations and may include intragastric members that are pre-loaded onto a delivery tube. In another embodiment, trigger wires or the like can be connected proximal to the overtube, wherein the trigger wires are used to expel the elastic band from the overtube.

The above-described intragastric members 911 may be withdrawn from the enclosed bag 930 by rupturing the bag 930. The relatively smaller intragastric members that are released from the bag may pass through the pylorus and gastrointestinal tract of the patient. The intragastric members can include a color coding to allow the intragastric members to be easily identified if the bag is prematurely ruptured. For example, the color coded intragastric members can provide notification to the physician or patient when identified in stool samples.

Alternatively, the above-described intragastric members can be removed by rupturing the bag 930 and utilizing an overtube to suction the intragastric members 911 from the bag and subsequently removing the bag through the overtube or endoscope with forceps or a similar device.

Having described the structures of the various intragastric members and bags, the loading of the intragastric bags into a delivery device, and the deployment of the loaded delivery device into the gastric lumen, an example of a method of treatment of obesity in mammals will now be discussed. An overtube 600 (FIG. 24) is positioned in the gastric lumen of the patient. After positioning the overtube 600 as shown in FIG. 24, a bag 30 may be advanced with a pusher rod (not shown) through the lumen of the overtube 600. The bag 30 is advanced through the lumen of the overtube 600 until it is positioned within the gastric lumen, as shown in FIG. 24.

With the bag positioned within the gastric lumen, one or more intragastric members 11 (FIG. 1) are loaded into a delivery tube 40 (FIG. 5). At least one intragastric member 11 may be compacted into a first configuration. The compacted intragastric member 11 is then loaded into a lumen 45 between a proximal end and distal end of a delivery tube 40 (FIG. 5). The intragastric members 11 may have openings 16 at the proximal end 13 and distal end 14 through which a retaining element 34 may extend to secure and connect intragastric members 11 to each other.

The delivery tube 40 may now be inserted into the bag 30. The delivery tube 40 is advanced through the overtube 600 until a distal end of the delivery tube 40 is positioned in the gastric lumen. At this juncture, the intragastric member 11 is manually pushed in a distal direction with a pusher member (not shown) so as to push the intragastric member 11 past the distal end of the delivery tube 40 and into the bag 30. The procedure may be repeated if more than one intragastric member 11 has been loaded into the delivery tube 40.

The intragastric members 11 expand from the compacted first configuration to the second configuration upon being pushed into the bag 30. The expansion may occur as the intragastric member 11 contacts fluid (e.g., saline or fluid of the gastric lumen). Alternatively, the intragastric member 11 may self-expand as it is pushed out of the delivery tube 40. The expansion may be sufficiently large to prevent the intragastric member from passing the mammal's pylorus. Alternatively, multiple intragastric members 11 may be grouped together via a tether 27 (FIG. 9) within the bag 30.

After all of the intragastric members 11 have been manually pushed out from the delivery tube 40 and into the interior of the bag 30 (FIG. 10) and expansion of the intragastric members 11 has occurred such that the overall volume of the bag 30 has increased, the proximal end of the bag 30 may be secured with a constraining element, such as a stopper 21 (FIG. 12), to prevent the intragastric members 11 from inadvertently falling out of the bag 30 (FIG. 11). The retaining element 34 may also be removed (FIG. 11). If desired, groupings 39 may be formed within the bag 30 by securing a coupling mechanism 26 to the bag 30. This enables cutting apart of the groupings 39 in order to facilitate removal of the intragastric members 11 when it is time to remove the intragastric members 11, 111, 211, 311 from the patient.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

The invention claimed is:

1. An intragastric device for the treatment of obesity, the intragastric device comprising:
   a non-inflatable bag comprising a substantially inelastic material disposed within the gastric lumen of a mammal, the bag comprising a constraining member; and
   a plurality of intragastric members disposed within the bag, the intragastric members being sufficiently small to permit introduction of the intragastric members into the bag, wherein a sufficient number of the intragastric members are disposed within the bag to prevent the bag from passing through the mammal's pylorus,
   wherein the intragastric members are enclosed within the bag by the constraining member.

2. The intragastric device according to claim 1, wherein the plurality of intragastric members are expandable from a first configuration to a second configuration.

3. The intragastric device according to claim 1, wherein the device further comprises a plurality of intragastric members connected together to facilitate delivery to the bag located in the gastric lumen.

4. The intragastric device according to claim 3, wherein the plurality of intragastric members are connected together with a retaining element that passes through an opening in each intragastric member, and further wherein said plurality of intragastric members are connected together in a first configuration.

5. The intragastric device according to claim 4, wherein the retaining element comprises a nylon thread having a first end and a second end that are connected together in the first configuration.

6. The intragastric member of claim 3, wherein the plurality of intragastric members are loaded through a delivery tube, wherein the delivery tube facilitates the delivery of the plurality of intragastric members from the delivery tube into the bag located in the gastric lumen.

7. The intragastric device according to claim 1 further comprising an overtube comprising a proximal end, a distal end and a lumen configured to receive the plurality of the intragastric members.

8. The intragastric device according to claim 1, wherein the bag comprises a plurality of openings along the surface of the bag to facilitate the passage of the gastric fluid into the bag.

9. The intragastric device of claim 1, wherein a constraining element is engaged to the bag to secure the plurality of the intragastric members within the bag.

10. The intragastric device according to claim 1, wherein the plurality of the intragastric members comprise a dissolvable outer package allowing the plurality of the intragastric members to expand from a first configuration to a second configuration.

11. The intragastric member according to claim 10, wherein the dissolvable outer package comprises a material selected from the group consisting of cellulose, gelatin and glycerin.

12. The intragastric device according to claim 1, wherein said plurality of the intragastric members comprise a nylon thread forming a bundle.

13. The intragastric device according to claim 1, wherein said plurality of the intragastric members comprise one or more elements selected from the group consisting of plastic, nylon, polyesters, polyurethanes, polyethylenes, polyamides, silicone and biocompatible polymers to which food will generally not adhere.

14. The intragastric device according to claim 1, wherein said plurality of the intragastric members comprise one or more elements selected from the group consisting of high-density polyethylene, low-density polyethylene, fluorinated ethylene propylene and ethylene vinyl acetate copolymer.

15. An intragastric device for the treatment of obesity, the intragastric device comprising:
   a non-inflatable bag comprising a substantially inelastic material having a plurality of openings distributed throughout an outer surface of the bag to facilitate the passage of the gastric fluid into and out of an interior of the bag;
   a plurality of intragastric members that are sufficiently small to permit introduction of the one or more intragastric members into the bag, wherein when the plurality of the intragastric members are disposed in the bag, the bag is configured to prevent the intragastric device from passing through the mammal's pylorus; a delivery tube having a lumen, a proximal end and a distal end, wherein the plurality of the intragastric members are loaded between the proximal end and distal end of the delivery tube; and an overtube comprising a proximal end, a distal end and a lumen configured to permit passage through the plurality of intragastric members.

16. The intragastric device of claim 15, wherein the plurality of intragastric members are expandable from a first configuration to a second configuration.

17. The intragastric device according to claim 16, wherein the intragastric device comprises a plurality of intragastric members connected together to facilitate delivery to the bag located in the gastric lumen.

18. The intragastric device according to claim 17, wherein the plurality of intragastric members are connected together with a retaining element that passes through an opening in each intragastric member, and further wherein the plurality of intragastric members are connected together in the first configuration.

19. The intragastric device according to claim 18, wherein the retaining element comprises a nylon thread having a first end and a second end that are connected together in the first configuration.

20. The intragastric device of claim 16, wherein a constraining element is engaged to the bag to secure the intragastric member within the bag.

21. The intragastric device according to claim 16, wherein said plurality of intragastric members comprise a dissolvable outer package allowing the intragastric member to expand from the first configuration to the second configuration.

22. The intragastric member according to claim 21, wherein the dissolvable outer package comprises a material selected from the group consisting of cellulose, gelatin and glycerin.

23. The intragastric device according to claim 16, wherein said plurality of intragastric members comprise one or more elements selected from the group consisting of plastic, nylon, polyesters, polyurethanes, polyethylenes, polyamides, silicone and biocompatible polymers to which food will generally not adhere.

* * * * *